US012648881B2

(12) United States Patent
Hartwell et al.

(10) Patent No.: US 12,648,881 B2
(45) Date of Patent: Jun. 9, 2026

(54) AUTOMATIC WOUND COUPLING DETECTION IN NEGATIVE PRESSURE WOUND THERAPY SYSTEMS

(71) Applicant: Smith & Nephew, Inc., Memphis, TN (US)

(72) Inventors: Edward Yerbury Hartwell, Hull (GB); Felix C. Quintanar, Hull (GB); Jason De Villiers, Cambridge (GB)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 18/107,882

(22) Filed: Feb. 9, 2023

(65) Prior Publication Data

US 2023/0190531 A1     Jun. 22, 2023

Related U.S. Application Data

(62) Division of application No. 16/300,449, filed as application No. PCT/US2017/032545 on May 12, 2017, now Pat. No. 11,602,461.

(Continued)

(51) Int. Cl.
*A61F 13/05* (2024.01)
*A61M 1/00* (2006.01)

(52) U.S. Cl.
CPC ............... *A61F 13/05* (2024.01); *A61M 1/96* (2021.05); *A61M 1/74* (2021.05); *A61M 1/90* (2021.05);

(Continued)

(58) Field of Classification Search
CPC ......... A61F 13/05; A61M 1/96; A61M 1/982; A61M 1/90; A61M 1/966; A61M 1/74
See application file for complete search history.

(56) References Cited

U.S. PATENT DOCUMENTS 695,270 A     3/1902  Beringer
3,194,239 A   7/1965  Sullivan et al.
(Continued)

FOREIGN PATENT DOCUMENTS

CN     102961815 A     3/2013
CN     104721892 A     6/2015
(Continued)

OTHER PUBLICATIONS

Cinterion., "Cinterion PHS8-P 3G HSPA+," retrieved from http://www.cinterion.com/tl_files/cinterion/downloads/cinterion_datasheet_PHSS_web.pdf, 2012, 2 pages.
(Continued)

*Primary Examiner* — Jessica Arble
*Assistant Examiner* — Arjuna P Chatrathi
(74) *Attorney, Agent, or Firm* — Knobbe, Martens, Olson & Bear, LLP

(57)     ABSTRACT

Embodiments of negative pressure wound therapy systems and methods for operating the systems are disclosed. In some embodiments, a system includes a negative pressure source, a sensor, and a controller. The negative pressure source can provide negative pressure via a fluid flow path to the wound dressing. The sensor can monitor pressure in the fluid flow path. The controller can determine whether the wound dressing is coupled to a wound from a change in magnitude of pressure in the fluid flow path over time being more indicative of a steady state condition than a chaotic condition while the negative pressure source maintains negative pressure in the fluid flow path within a pressure range. In addition, the controller can output a first indication denoting that the wound dressing is coupled to the wound and a second indication denoting that the wound dressing is not coupled to the wound.

19 Claims, 19 Drawing Sheets

WOUND COUPLING DETECTION PROCESS

Related U.S. Application Data

(60) Provisional application No. 62/378,856, filed on Aug. 24, 2016, provisional application No. 62/335,978, filed on May 13, 2016.

(52) U.S. Cl.
CPC ............. *A61M 1/966* (2021.05); *A61M 1/982* (2021.05); *A61M 2205/13* (2013.01); *A61M 2205/3344* (2013.01); *A61M 2205/52* (2013.01)

(56) References Cited

U.S. PATENT DOCUMENTS

| | | | |
|---|---|---|---|
| 4,832,299 A | 5/1989 | Gorton et al. | |
| 5,161,525 A | 11/1992 | Kimm et al. | |
| 5,219,428 A | 6/1993 | Stern | |
| 5,449,347 A | 9/1995 | Preen et al. | |
| 5,466,229 A | 11/1995 | Elson et al. | |
| 5,473,536 A | 12/1995 | Wimmer | |
| 5,582,601 A | 12/1996 | Wortrich et al. | |
| 5,584,824 A | 12/1996 | Gillette et al. | |
| 5,622,429 A | 4/1997 | Heinze | |
| 5,656,027 A | 8/1997 | Ellingboe | |
| 5,669,892 A | 9/1997 | Keogh et al. | |
| 5,693,013 A | 12/1997 | Geuder | |
| 5,960,403 A | 9/1999 | Brown | |
| 5,989,234 A | 11/1999 | Valerio et al. | |
| 6,055,506 A | 4/2000 | Frasca et al. | |
| 6,174,306 B1 | 1/2001 | Fleischmann | |
| 6,240,921 B1 * | 6/2001 | Brydon ............... | A61M 16/024 128/205.25 |
| 6,241,739 B1 | 6/2001 | Waldron | |
| 6,336,900 B1 | 1/2002 | Alleckson et al. | |
| 6,353,445 B1 | 3/2002 | Babula et al. | |
| 6,375,614 B1 | 4/2002 | Braun et al. | |
| 6,385,622 B2 | 5/2002 | Bouve et al. | |
| 6,406,426 B1 | 6/2002 | Reuss et al. | |
| 6,434,572 B2 | 8/2002 | Derzay et al. | |
| 6,460,041 B2 | 10/2002 | Lloyd | |
| 6,572,530 B1 | 6/2003 | Araki et al. | |
| 6,574,518 B1 | 6/2003 | Lounsberry et al. | |
| 6,605,032 B2 | 8/2003 | Benkowski et al. | |
| 6,640,145 B2 | 10/2003 | Hoffberg et al. | |
| 6,640,246 B1 | 10/2003 | Gary et al. | |
| 6,675,131 B2 | 1/2004 | Hahn | |
| 6,681,003 B2 | 1/2004 | Linder et al. | |
| 6,723,046 B2 | 4/2004 | Lichtenstein et al. | |
| 6,747,556 B2 | 6/2004 | Medema et al. | |
| 6,755,807 B2 | 6/2004 | Risk, Jr. et al. | |
| 6,779,024 B2 | 8/2004 | DeLahuerga | |
| 6,782,285 B2 | 8/2004 | Birkenbach et al. | |
| 6,856,825 B2 | 2/2005 | Hahn | |
| 6,868,528 B2 | 3/2005 | Roberts | |
| 6,871,211 B2 | 3/2005 | Labounty et al. | |
| 6,909,974 B2 | 6/2005 | Yung et al. | |
| 6,912,481 B2 | 6/2005 | Breunissen et al. | |
| 6,961,731 B2 | 11/2005 | Holbrook | |
| 7,004,915 B2 | 2/2006 | Boynton et al. | |
| 7,022,113 B2 | 4/2006 | Lockwood et al. | |
| 7,051,012 B2 | 5/2006 | Cole et al. | |
| 7,062,251 B2 | 6/2006 | Birkett et al. | |
| 7,066,883 B2 | 6/2006 | Schmidt et al. | |
| 7,103,578 B2 | 9/2006 | Beck et al. | |
| 7,108,683 B2 | 9/2006 | Zamierowski | |
| 7,120,488 B2 | 10/2006 | Nova et al. | |
| 7,128,735 B2 | 10/2006 | Weston | |
| 7,133,869 B2 | 11/2006 | Bryan et al. | |
| 7,167,858 B2 | 1/2007 | Naeymi-Rad et al. | |
| 7,212,829 B1 | 5/2007 | Lau et al. | |
| 7,264,591 B2 | 9/2007 | Brown | |
| 7,304,573 B2 | 12/2007 | Postma | |
| 7,311,665 B2 | 12/2007 | Hawthorne et al. | |
| 7,333,002 B2 | 2/2008 | Bixler et al. | |
| 7,353,179 B2 | 4/2008 | Ott et al. | |
| 7,361,184 B2 | 4/2008 | Joshi | |
| 7,384,267 B1 | 6/2008 | Franks et al. | |
| 7,430,598 B2 | 9/2008 | Raden et al. | |
| 7,430,608 B2 | 9/2008 | Noonan et al. | |
| 7,438,705 B2 | 10/2008 | Karpowicz et al. | |
| 7,451,002 B2 | 11/2008 | Choubey | |
| 7,457,804 B2 | 11/2008 | Uber et al. | |
| 7,460,872 B2 | 12/2008 | Millard et al. | |
| 7,534,240 B1 | 5/2009 | Johnson | |
| 7,553,306 B1 | 6/2009 | Hunt et al. | |
| 7,569,742 B2 | 8/2009 | Haggstrom et al. | |
| 7,598,855 B2 | 10/2009 | Scalisi et al. | |
| 7,615,036 B2 | 11/2009 | Joshi et al. | |
| 7,627,334 B2 | 12/2009 | Cohen et al. | |
| 7,649,449 B2 | 1/2010 | Fenske et al. | |
| 7,670,323 B2 | 3/2010 | Hunt et al. | |
| 7,671,733 B2 | 3/2010 | McNeal et al. | |
| 7,684,999 B2 | 3/2010 | Brown | |
| 7,698,156 B2 | 4/2010 | Martucci et al. | |
| 7,699,823 B2 | 4/2010 | Haggstrom et al. | |
| 7,723,560 B2 | 5/2010 | Lockwood et al. | |
| 7,734,764 B2 | 6/2010 | Weiner et al. | |
| 7,749,164 B2 | 7/2010 | Davis | |
| 7,758,555 B2 | 7/2010 | Kelch et al. | |
| 7,776,028 B2 | 8/2010 | Miller et al. | |
| 7,779,153 B2 | 8/2010 | Van den Heuvel et al. | |
| 7,789,828 B2 | 9/2010 | Clapp | |
| 7,794,438 B2 | 9/2010 | Henley et al. | |
| 7,827,148 B2 | 11/2010 | Mori et al. | |
| 7,846,141 B2 | 12/2010 | Weston | |
| 7,857,806 B2 | 12/2010 | Karpowicz et al. | |
| 7,862,339 B2 | 1/2011 | Mulligan | |
| 7,865,375 B2 | 1/2011 | Lancaster et al. | |
| 7,889,069 B2 | 2/2011 | Fifolt et al. | |
| 7,890,887 B1 | 2/2011 | Linardos et al. | |
| 7,912,823 B2 | 3/2011 | Ferrari et al. | |
| 7,925,603 B1 | 4/2011 | Laidig et al. | |
| 7,927,319 B2 | 4/2011 | Lawhorn | |
| 7,976,519 B2 | 7/2011 | Bubb et al. | |
| 7,981,098 B2 | 7/2011 | Boehringer et al. | |
| 7,988,850 B2 | 8/2011 | Roncadi et al. | |
| 8,015,443 B2 | 9/2011 | Adachi | |
| 8,015,972 B2 | 9/2011 | Pirzada | |
| 8,019,618 B2 | 9/2011 | Brown | |
| 8,036,925 B2 | 10/2011 | Choubey | |
| 8,048,046 B2 | 11/2011 | Hudspeth et al. | |
| 8,054,950 B1 | 11/2011 | Hung et al. | |
| 8,061,360 B2 | 11/2011 | Locke et al. | |
| 8,069,057 B2 | 11/2011 | Choubey et al. | |
| 8,094,009 B2 | 1/2012 | Allen et al. | |
| 8,105,295 B2 | 1/2012 | Blott et al. | |
| 8,126,735 B2 | 2/2012 | Dicks et al. | |
| 8,130,095 B2 | 3/2012 | Allen et al. | |
| 8,131,472 B2 | 3/2012 | Chow et al. | |
| 8,167,869 B2 | 5/2012 | Wudyka | |
| 8,180,750 B2 | 5/2012 | Wilmering et al. | |
| 8,190,445 B2 | 5/2012 | Kuth et al. | |
| 8,190,448 B2 | 5/2012 | Bajars et al. | |
| 8,228,188 B2 | 7/2012 | Key et al. | |
| 8,246,606 B2 | 8/2012 | Stevenson et al. | |
| 8,249,894 B2 | 8/2012 | Brown | |
| 8,255,241 B2 | 8/2012 | Cafer | |
| 8,257,328 B2 | 9/2012 | Augustine et al. | |
| 8,260,630 B2 | 9/2012 | Brown | |
| 8,267,918 B2 | 9/2012 | Johnson et al. | |
| 8,280,682 B2 | 10/2012 | Vock et al. | |
| 8,284,046 B2 | 10/2012 | Allen et al. | |
| 8,290,792 B2 | 10/2012 | Sekura | |
| 8,291,337 B2 | 10/2012 | Gannin et al. | |
| 8,294,586 B2 | 10/2012 | Pidgeon et al. | |
| 8,308,714 B2 | 11/2012 | Weston et al. | |
| 8,317,774 B2 | 11/2012 | Adahan | |
| 8,323,263 B2 | 12/2012 | Wood et al. | |
| 8,332,233 B2 | 12/2012 | Ott et al. | |
| 8,333,744 B2 | 12/2012 | Hartwell et al. | |
| 8,334,768 B2 | 12/2012 | Eaton et al. | |
| 8,337,482 B2 | 12/2012 | Wood et al. | |
| 8,360,975 B1 | 1/2013 | Schwieterman et al. | |
| 8,366,690 B2 | 2/2013 | Locke et al. | |

(56)     References Cited

U.S. PATENT DOCUMENTS

| | | | |
|---|---|---|---|
| 8,400,295 B1 | 3/2013 | Khaira |
| 8,409,170 B2 | 4/2013 | Locke et al. |
| 8,422,377 B2 | 4/2013 | Weiner et al. |
| 8,424,517 B2 | 4/2013 | Sutherland et al. |
| 8,436,871 B2 | 5/2013 | Alberte |
| 8,439,882 B2 | 5/2013 | Kelch |
| 8,449,508 B2 | 5/2013 | Coulthard et al. |
| 8,457,740 B2 | 6/2013 | Osche |
| 8,460,257 B2 | 6/2013 | Locke et al. |
| 8,480,641 B2 | 7/2013 | Jacobs |
| 8,494,349 B2 | 7/2013 | Gordon |
| 8,515,776 B2 | 8/2013 | Schoenberg |
| 8,532,764 B2 | 9/2013 | Duke |
| 8,540,688 B2 | 9/2013 | Eckstein et al. |
| 8,545,483 B2 | 10/2013 | Schwabe et al. |
| 8,554,195 B2 | 10/2013 | Rao |
| 8,554,902 B2 | 10/2013 | Ebert et al. |
| 8,558,964 B2 | 10/2013 | Bedingfield |
| 8,560,082 B2 | 10/2013 | Wei |
| 8,577,694 B2 | 11/2013 | Kanaan |
| 8,595,553 B2 | 11/2013 | Goertler et al. |
| 8,600,777 B2 | 12/2013 | Schoenberg et al. |
| 8,617,129 B2 | 12/2013 | Hartwell |
| 8,622,981 B2 | 1/2014 | Hartwell et al. |
| 8,626,342 B2 | 1/2014 | Williams et al. |
| 8,626,526 B2 | 1/2014 | Lemke et al. |
| 8,630,660 B2 | 1/2014 | Ray et al. |
| 8,632,485 B2 | 1/2014 | Schlaeper et al. |
| 8,659,420 B2 | 2/2014 | Salvat et al. |
| 8,668,677 B2 | 3/2014 | Eckstein et al. |
| 8,676,597 B2 | 3/2014 | Buehler et al. |
| 8,689,008 B2 | 4/2014 | Rangadass et al. |
| 8,694,600 B2 | 4/2014 | Gaines et al. |
| 8,706,537 B1 | 4/2014 | Young et al. |
| 8,725,528 B2 | 5/2014 | Locke et al. |
| 8,756,078 B2 | 6/2014 | Collins, Jr. et al. |
| 8,757,485 B2 | 6/2014 | Drees et al. |
| 8,758,315 B2 | 6/2014 | Chen et al. |
| 8,768,441 B2 | 7/2014 | De Zwart et al. |
| 8,769,625 B2 | 7/2014 | Wang et al. |
| 8,781,847 B2 | 7/2014 | Simms et al. |
| 8,795,171 B2 | 8/2014 | Adamczyk |
| 8,795,244 B2 | 8/2014 | Randolph et al. |
| 8,814,840 B2 | 8/2014 | Evans et al. |
| 8,814,841 B2 | 8/2014 | Hartwell |
| 8,814,842 B2 | 8/2014 | Coulthard et al. |
| 8,827,983 B2 | 9/2014 | Braga et al. |
| 8,838,136 B2 | 9/2014 | Carnes et al. |
| 8,843,327 B2 | 9/2014 | Vernon-Harcourt et al. |
| 8,845,603 B2 | 9/2014 | Middleton et al. |
| 8,858,517 B2 | 10/2014 | Pan et al. |
| 8,862,393 B2 | 10/2014 | Zhou et al. |
| 8,868,794 B2 | 10/2014 | Masoud et al. |
| 8,874,035 B2 | 10/2014 | Sherman et al. |
| 8,887,100 B1 | 11/2014 | Cook et al. |
| 8,890,656 B2 | 11/2014 | Pendse |
| 8,897,198 B2 | 11/2014 | Gaines et al. |
| 8,902,278 B2 | 12/2014 | Pinter et al. |
| 8,905,985 B2 | 12/2014 | Allen et al. |
| 8,909,595 B2 | 12/2014 | Gandy et al. |
| 8,912,897 B2 | 12/2014 | Carnes |
| 8,922,377 B2 | 12/2014 | Carnes |
| 8,945,030 B2 | 2/2015 | Weston |
| 8,945,073 B2 | 2/2015 | Croizat et al. |
| 8,945,074 B2 | 2/2015 | Buan et al. |
| 8,947,237 B2 | 2/2015 | Margon et al. |
| 8,974,429 B2 | 3/2015 | Gordon et al. |
| 8,978,026 B2 | 3/2015 | Charlton et al. |
| 8,996,393 B2 | 3/2015 | Sobie |
| 9,017,286 B2 | 4/2015 | Kamen et al. |
| 9,047,648 B1 | 6/2015 | Lekutai et al. |
| 9,058,634 B2 | 6/2015 | Buan et al. |
| 9,081,885 B2 | 7/2015 | Bangera et al. |
| 9,084,845 B2 | 7/2015 | Adie et al. |
| 9,087,141 B2 | 7/2015 | Huang et al. |
| 9,092,705 B2 | 7/2015 | Zhuang |
| 9,098,114 B2 | 8/2015 | Potter et al. |
| 9,105,006 B2 | 8/2015 | Williamson |
| 9,135,398 B2 | 9/2015 | Kaib et al. |
| 9,141,270 B1 | 9/2015 | Stuart et al. |
| 9,159,148 B2 | 10/2015 | Boyer et al. |
| 9,215,516 B2 | 12/2015 | Carnes et al. |
| 9,215,581 B2 | 12/2015 | Julian et al. |
| 9,230,420 B2 | 1/2016 | Lee et al. |
| 9,268,827 B2 | 2/2016 | Fernandez |
| 9,286,443 B2 | 3/2016 | Ford et al. |
| 9,323,893 B2 | 4/2016 | Berry et al. |
| 9,326,683 B2 | 5/2016 | Ganapathy et al. |
| 9,332,363 B2 | 5/2016 | Jain et al. |
| 9,338,819 B2 | 5/2016 | Meng et al. |
| 9,408,954 B2 | 8/2016 | Gordon et al. |
| 9,424,020 B2 | 8/2016 | Borges et al. |
| 9,427,159 B2 | 8/2016 | Chang |
| 9,436,645 B2 | 9/2016 | Al-Ali et al. |
| 9,436,800 B2 | 9/2016 | Forrester |
| 9,439,584 B1 | 9/2016 | De Vries et al. |
| 9,460,431 B2 | 10/2016 | Curry |
| 9,483,614 B2 | 11/2016 | Ash et al. |
| 9,539,373 B2 | 1/2017 | Jones et al. |
| 9,545,466 B2 | 1/2017 | Locke et al. |
| 9,558,331 B2 | 1/2017 | Orona et al. |
| 9,585,565 B2 | 3/2017 | Carnes |
| 9,589,247 B2 | 3/2017 | Bolene et al. |
| 9,602,952 B2 | 3/2017 | Kang et al. |
| 9,610,388 B2 | 4/2017 | Aceto et al. |
| 9,636,440 B2 | 5/2017 | Weston et al. |
| 9,658,066 B2 | 5/2017 | Yuen et al. |
| 9,662,438 B2 | 5/2017 | Kamen et al. |
| 9,681,993 B2 | 6/2017 | Wu et al. |
| 9,687,618 B2 | 6/2017 | Steinhauer et al. |
| 9,693,691 B2 | 7/2017 | Johnson |
| 9,716,757 B2 | 7/2017 | Fernandes |
| 9,740,825 B2 | 8/2017 | Sansale et al. |
| 9,741,084 B2 | 8/2017 | Holmes et al. |
| 9,787,842 B1 | 10/2017 | Brooksby et al. |
| 9,792,660 B2 | 10/2017 | Cannon et al. |
| 9,817,948 B2 | 11/2017 | Swank |
| 9,818,164 B2 | 11/2017 | Nolte et al. |
| 9,838,645 B2 | 12/2017 | Hyde et al. |
| 9,864,066 B2 | 1/2018 | Park et al. |
| 9,878,081 B2 | 1/2018 | Leiendecker et al. |
| 9,901,664 B2 | 2/2018 | Askem |
| 9,928,478 B2 | 3/2018 | Ragusky et al. |
| 9,974,492 B1 | 5/2018 | Dicks et al. |
| 9,990,466 B2 | 6/2018 | DeBusk et al. |
| 9,996,681 B2 | 6/2018 | Suarez et al. |
| 10,046,096 B2 | 8/2018 | Askem et al. |
| 10,049,346 B2 | 8/2018 | Jensen et al. |
| 10,061,894 B2 | 8/2018 | Sethumadhavan et al. |
| 10,127,357 B2 | 11/2018 | Whiting et al. |
| 10,152,575 B2 | 12/2018 | Sexton et al. |
| 10,173,008 B2 | 1/2019 | Simpson et al. |
| 10,185,834 B2 | 1/2019 | Adam et al. |
| 10,328,188 B2 | 6/2019 | Deutsch et al. |
| 11,602,461 B2 * | 3/2023 | Hartwell ................ A61F 13/05 |
| 2001/0013822 A1 | 8/2001 | Nazarian et al. |
| 2001/0031944 A1 | 10/2001 | Peterson et al. |
| 2002/0013516 A1 | 1/2002 | Freyre et al. |
| 2002/0026160 A1 | 2/2002 | Takahashi et al. |
| 2002/0082568 A1 | 6/2002 | Yam |
| 2002/0087360 A1 | 7/2002 | Pettit |
| 2002/0128804 A1 | 9/2002 | Geva |
| 2002/0128869 A1 | 9/2002 | Kuth |
| 2002/0135336 A1 | 9/2002 | Zhou et al. |
| 2002/0177757 A1 | 11/2002 | Britton |
| 2002/0184055 A1 | 12/2002 | Naghavi et al. |
| 2002/0193679 A1 | 12/2002 | Malave et al. |
| 2002/0198504 A1 | 12/2002 | Risk, Jr. et al. |
| 2002/0198505 A1 | 12/2002 | Want et al. |
| 2003/0009244 A1 | 1/2003 | Engleson et al. |
| 2003/0018736 A1 | 1/2003 | Christ et al. |
| 2003/0028175 A1 | 2/2003 | D'Antonio |
| 2003/0093041 A1 | 5/2003 | Risk, Jr. et al. |
| 2003/0105649 A1 | 6/2003 | Sheiner et al. |

(56)                    References Cited

U.S. PATENT DOCUMENTS

2003/0128125 A1    7/2003   Burbank et al.
2003/0164600 A1    9/2003   Dunn et al.
2003/0182158 A1    9/2003   Son
2003/0214412 A1   11/2003   Ho et al.
2003/0221687 A1   12/2003   Kaigler
2003/0229518 A1   12/2003   Abraham-Fuchs et al.
2004/0006492 A1    1/2004   Watanabe
2004/0039255 A1    2/2004   Simonsen et al.
2004/0054338 A1    3/2004   Bybordi et al.
2004/0054775 A1    3/2004   Poliac et al.
2004/0059284 A1    3/2004   Nash et al.
2004/0064132 A1    4/2004   Boehringer et al.
2004/0078223 A1    4/2004   Sacco et al.
2004/0102743 A1    5/2004   Walker
2004/0120825 A1*   6/2004   Bouton ................ A61M 5/365
                                                        417/44.2
2004/0143458 A1    7/2004   Pulkkinen et al.
2004/0167802 A1    8/2004   Takada et al.
2004/0167804 A1    8/2004   Simpson et al.
2004/0171982 A1    9/2004   Danchin
2004/0172301 A1    9/2004   Mihai et al.
2004/0181314 A1    9/2004   Zaleski
2004/0181433 A1    9/2004   Blair
2004/0193449 A1    9/2004   Wildman et al.
2004/0204962 A1   10/2004   Howser et al.
2005/0011282 A1    1/2005   Voege et al.
2005/0033124 A1    2/2005   Kelly et al.
2005/0055225 A1    3/2005   Mehl
2005/0055242 A1    3/2005   Bello et al.
2005/0055244 A1    3/2005   Mullan et al.
2005/0060211 A1    3/2005   Xiao et al.
2005/0065471 A1    3/2005   Kuntz
2005/0065817 A1    3/2005   Mihai et al.
2005/0097200 A1    5/2005   Denning, Jr. et al.
2005/0102167 A1    5/2005   Kapoor
2005/0108046 A1    5/2005   Craft
2005/0108057 A1    5/2005   Cohen et al.
2005/0114176 A1    5/2005   Dominick et al.
2005/0119914 A1    6/2005   Batch
2005/0124966 A1    6/2005   Karpowicz et al.
2005/0187528 A1    8/2005   Berg
2005/0209560 A1    9/2005   Boukhny et al.
2005/0222873 A1   10/2005   Nephin et al.
2005/0240111 A1   10/2005   Chung
2005/0256447 A1   11/2005   Richardson et al.
2005/0261805 A1   11/2005   Mori et al.
2005/0283382 A1   12/2005   Donoghue et al.
2006/0004604 A1    1/2006   White
2006/0029675 A1    2/2006   Ginther
2006/0064323 A1    3/2006   Alleckson et al.
2006/0085393 A1    4/2006   Modesitt
2006/0089539 A1    4/2006   Miodownik et al.
2006/0095853 A1    5/2006   Amyot et al.
2006/0144440 A1    7/2006   Merkle
2006/0149171 A1    7/2006   Vogel et al.
2006/0155584 A1    7/2006   Aggarwal
2006/0161460 A1    7/2006   Smitherman et al.
2006/0173253 A1*   8/2006   Ganapathy .............. A61M 1/95
                                                        607/88
2006/0190130 A1    8/2006   Fedor et al.
2006/0195843 A1    8/2006   Hall
2006/0224051 A1   10/2006   Teller et al.
2006/0229557 A1   10/2006   Fathallah et al.
2006/0246922 A1   11/2006   Gasbarro et al.
2007/0005029 A1    1/2007   Hopkins et al.
2007/0016152 A1    1/2007   Karpowicz et al.
2007/0032741 A1    2/2007   Hibner et al.
2007/0032762 A1    2/2007   Vogel
2007/0032763 A1    2/2007   Vogel
2007/0055209 A1    3/2007   Patel et al.
2007/0078444 A1    4/2007   Larsson
2007/0118096 A1    5/2007   Smith et al.
2007/0136099 A1    6/2007   Neligh et al.
2007/0156456 A1    7/2007   Mcgillin et al.
2007/0179460 A1    8/2007   Adahan 2007/0180904 A1    8/2007   Gao
2007/0197881 A1    8/2007   Wolf et al.
2007/0219480 A1    9/2007   Kamen et al.
2007/0219826 A1    9/2007   Brodsky et al.
2007/0255116 A1   11/2007   Mehta et al.
2007/0260226 A1   11/2007   Jaeb et al.
2007/0271298 A1   11/2007   Juang et al.
2008/0005000 A1*   1/2008   Radl ...................... G07F 17/06
                                                        705/34
2008/0009681 A1    1/2008   Al Hussiny
2008/0015526 A1    1/2008   Reiner et al.
2008/0041401 A1    2/2008   Casola et al.
2008/0051708 A1    2/2008   Kumar et al.
2008/0071209 A1    3/2008   Moubayed et al.
2008/0082040 A1    4/2008   Kubler et al.
2008/0082077 A1    4/2008   Williams
2008/0086357 A1    4/2008   Choubey et al.
2008/0091175 A1    4/2008   Frikart et al.
2008/0091659 A1    4/2008   McFaul
2008/0119705 A1    5/2008   Patel et al.
2008/0125697 A1    5/2008   Gao
2008/0125698 A1    5/2008   Gerg et al.
2008/0126126 A1    5/2008   Ballai
2008/0140160 A1    6/2008   Goetz et al.
2008/0167534 A1    7/2008   Young et al.
2008/0177579 A1    7/2008   Dehaan
2008/0200905 A1    8/2008   Heaton et al.
2008/0200906 A1    8/2008   Sanders et al.
2008/0221396 A1    9/2008   Garces et al.
2008/0242945 A1   10/2008   Gugliotti et al.
2008/0243096 A1   10/2008   Svedman
2008/0312953 A1   12/2008   Claus
2009/0005746 A1    1/2009   Nielsen et al.
2009/0037216 A1    2/2009   Bluemler et al.
2009/0037220 A1    2/2009   Chambers et al.
2009/0043268 A1    2/2009   Eddy et al.
2009/0048492 A1    2/2009   Rantala et al.
2009/0048865 A1    2/2009   Breazeale, Jr.
2009/0088823 A1    4/2009   Barak et al.
2009/0097623 A1    4/2009   Bharadwaj
2009/0099866 A1    4/2009   Newman
2009/0099867 A1    4/2009   Newman
2009/0101219 A1    4/2009   Martini et al.
2009/0115663 A1    5/2009   Brown et al.
2009/0118591 A1    5/2009   Kim et al.
2009/0125331 A1    5/2009   Pamsgaard et al.
2009/0136909 A1    5/2009   Asukai et al.
2009/0144091 A1    6/2009   Rago
2009/0157429 A1    6/2009   Lee et al.
2009/0163774 A1    6/2009   Thatha et al.
2009/0171166 A1    7/2009   Amundson et al.
2009/0177495 A1    7/2009   Abousy et al.
2009/0187424 A1    7/2009   Grabowski
2009/0204434 A1    8/2009   Breazeale, Jr.
2009/0204435 A1    8/2009   Gale
2009/0205042 A1    8/2009   Zhou et al.
2009/0206017 A1    8/2009   Rohde et al.
2009/0224889 A1    9/2009   Aggarwal et al.
2009/0270833 A1   10/2009   DeBelser et al.
2009/0281822 A1   11/2009   Warner et al.
2009/0281830 A1   11/2009   Mcnames et al.
2009/0281867 A1   11/2009   Sievenpiper et al.
2009/0299306 A1   12/2009   Buan
2009/0326339 A1   12/2009   Horvitz
2009/0327102 A1   12/2009   Maniar et al.
2010/0001838 A1    1/2010   Miodownik et al.
2010/0017471 A1    1/2010   Brown et al.
2010/0022848 A1    1/2010   Lee et al.
2010/0022990 A1    1/2010   Karpowicz et al.
2010/0030302 A1    2/2010   Blowers et al.
2010/0036333 A1    2/2010   Schenk, III et al.
2010/0042021 A1    2/2010   Hu et al.
2010/0069829 A1    3/2010   Hutchinson et al.
2010/0090004 A1    4/2010   Sands et al.
2010/0106528 A1    4/2010   Brackett et al.
2010/0113908 A1    5/2010   Vargas et al.
2010/0114026 A1    5/2010   Karratt et al.
2010/0121257 A1    5/2010   King
2010/0126268 A1    5/2010   Baily et al.

(56) References Cited

U.S. PATENT DOCUMENTS

| | | | |
|---|---|---|---|
| 2010/0137775 A1 | 6/2010 | Hu et al. |
| 2010/0145161 A1 | 6/2010 | Niyato et al. |
| 2010/0145289 A1 | 6/2010 | Lina et al. |
| 2010/0150991 A1 | 6/2010 | Bernstein |
| 2010/0191178 A1 | 7/2010 | Ross et al. |
| 2010/0200486 A1 | 8/2010 | Guenther et al. |
| 2010/0211030 A1 | 8/2010 | Turner et al. |
| 2010/0222645 A1 | 9/2010 | Nadler et al. |
| 2010/0234708 A1 | 9/2010 | Buck et al. |
| 2010/0255876 A1 | 10/2010 | Jordan et al. |
| 2010/0280435 A1 | 11/2010 | Raney et al. |
| 2010/0280536 A1 | 11/2010 | Hartwell |
| 2010/0305523 A1 | 12/2010 | Vess |
| 2010/0313958 A1 | 12/2010 | Patel et al. |
| 2010/0318043 A1 | 12/2010 | Malhi et al. |
| 2010/0318071 A1 | 12/2010 | Wudyka |
| 2011/0004188 A1 | 1/2011 | Shekalim |
| 2011/0008179 A1 | 1/2011 | Turner et al. |
| 2011/0009824 A1 | 1/2011 | Yodfat et al. |
| 2011/0015587 A1 | 1/2011 | Tumey et al. |
| 2011/0015590 A1 | 1/2011 | Svedman et al. |
| 2011/0015593 A1* | 1/2011 | Svedman ................ A61M 1/74 |
| | | 604/319 |
| 2011/0028881 A1 | 2/2011 | Basaglia |
| 2011/0028882 A1 | 2/2011 | Basaglia |
| 2011/0028921 A1 | 2/2011 | Hartwell et al. |
| 2011/0034861 A1 | 2/2011 | Schaefer |
| 2011/0038741 A1 | 2/2011 | Lissner et al. |
| 2011/0040288 A1 | 2/2011 | Eckstein et al. |
| 2011/0054810 A1 | 3/2011 | Turner et al. |
| 2011/0063117 A1 | 3/2011 | Turner et al. |
| 2011/0066096 A1 | 3/2011 | Svedman |
| 2011/0066110 A1 | 3/2011 | Fathallah et al. |
| 2011/0066123 A1 | 3/2011 | Tout et al. |
| 2011/0071415 A1 | 3/2011 | Karwoski et al. |
| 2011/0071844 A1 | 3/2011 | Cannon et al. |
| 2011/0073107 A1 | 3/2011 | Rodman et al. |
| 2011/0092927 A1 | 4/2011 | Wilkes et al. |
| 2011/0092958 A1 | 4/2011 | Jacobs |
| 2011/0106028 A1 | 5/2011 | Giezendanner et al. |
| 2011/0106561 A1 | 5/2011 | Eaton, Jr. et al. |
| 2011/0112857 A1 | 5/2011 | Yurko et al. |
| 2011/0130712 A1 | 6/2011 | Topaz |
| 2011/0137759 A1 | 6/2011 | Wellington et al. |
| 2011/0145018 A1 | 6/2011 | Fotsch et al. |
| 2011/0173028 A1 | 7/2011 | Bond |
| 2011/0178481 A1 | 7/2011 | Locke et al. |
| 2011/0184754 A1 | 7/2011 | Park et al. |
| 2011/0196321 A1 | 8/2011 | Wudyka |
| 2011/0225008 A1 | 9/2011 | Elkouh et al. |
| 2011/0245682 A1 | 10/2011 | Robinson et al. |
| 2011/0246219 A1 | 10/2011 | Smith et al. |
| 2011/0251569 A1 | 10/2011 | Turner et al. |
| 2011/0257572 A1 | 10/2011 | Locke et al. |
| 2011/0275353 A1 | 11/2011 | Liu |
| 2011/0288511 A1 | 11/2011 | Locke et al. |
| 2011/0288878 A1 | 11/2011 | Blair |
| 2011/0313789 A1 | 12/2011 | Kamen et al. |
| 2012/0001762 A1 | 1/2012 | Turner et al. |
| 2012/0016322 A1 | 1/2012 | Coulthard et al. |
| 2012/0029312 A1 | 2/2012 | Beaudry et al. |
| 2012/0029313 A1 | 2/2012 | Burdett et al. |
| 2012/0032819 A1 | 2/2012 | Chae et al. |
| 2012/0035427 A1 | 2/2012 | Friedman et al. |
| 2012/0035560 A1 | 2/2012 | Eddy et al. |
| 2012/0035561 A1 | 2/2012 | Locke et al. |
| 2012/0046625 A1 | 2/2012 | Johannison |
| 2012/0071845 A1 | 3/2012 | Hu et al. |
| 2012/0077605 A1 | 3/2012 | Nakagaito et al. |
| 2012/0081225 A1 | 4/2012 | Waugh et al. |
| 2012/0089369 A1 | 4/2012 | Abuzeni et al. |
| 2012/0123323 A1 | 5/2012 | Kagan et al. |
| 2012/0123358 A1 | 5/2012 | Hall et al. |
| 2012/0123796 A1 | 5/2012 | Mcfaul |
| 2012/0157889 A1 | 6/2012 | Tanis et al. |
| 2012/0157941 A1 | 6/2012 | Luckemeyer et al. |
| 2012/0181405 A1 | 7/2012 | Zlatic et al. |
| 2012/0182143 A1 | 7/2012 | Gaines et al. |
| 2012/0184930 A1 | 7/2012 | Johannison |
| 2012/0184932 A1 | 7/2012 | Giezendanner et al. |
| 2012/0191475 A1 | 7/2012 | Pandey |
| 2012/0197196 A1 | 8/2012 | Halbert et al. |
| 2012/0209226 A1 | 8/2012 | Simmons et al. |
| 2012/0212455 A1 | 8/2012 | Kloeffel |
| 2012/0215455 A1 | 8/2012 | Patil et al. |
| 2012/0220960 A1 | 8/2012 | Ruland |
| 2012/0226247 A1 | 9/2012 | Danei et al. |
| 2012/0259283 A1 | 10/2012 | Haase |
| 2012/0259651 A1 | 10/2012 | Mallon et al. |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2012/0290217 A1 | 11/2012 | Shoval et al. |
| 2012/0295566 A1 | 11/2012 | Collins et al. |
| 2012/0310205 A1 | 12/2012 | Lee et al. |
| 2013/0018355 A1 | 1/2013 | Brand et al. |
| 2013/0023719 A1 | 1/2013 | Bennett |
| 2013/0028788 A1 | 1/2013 | Gronau et al. |
| 2013/0030394 A1 | 1/2013 | Locke et al. |
| 2013/0035615 A1 | 2/2013 | Hsieh |
| 2013/0045764 A1 | 2/2013 | Vik et al. |
| 2013/0062265 A1 | 3/2013 | Balschat et al. |
| 2013/0066285 A1 | 3/2013 | Locke et al. |
| 2013/0073303 A1 | 3/2013 | Hsu |
| 2013/0076528 A1 | 3/2013 | Boettner et al. |
| 2013/0085462 A1 | 4/2013 | Nip et al. |
| 2013/0087609 A1 | 4/2013 | Nichol et al. |
| 2013/0090949 A1 | 4/2013 | Tibebu |
| 2013/0103419 A1 | 4/2013 | Beaudry |
| 2013/0124227 A1 | 5/2013 | Ellis |
| 2013/0132855 A1 | 5/2013 | Manicka et al. |
| 2013/0144227 A1 | 6/2013 | Locke et al. |
| 2013/0150686 A1 | 6/2013 | Fronterhouse et al. |
| 2013/0150698 A1 | 6/2013 | Hsu et al. |
| 2013/0151274 A1 | 6/2013 | Bage et al. |
| 2013/0157571 A1 | 6/2013 | Wondka et al. |
| 2013/0159456 A1 | 6/2013 | Daoud et al. |
| 2013/0160082 A1 | 6/2013 | Miller |
| 2013/0165821 A1 | 6/2013 | Freedman et al. |
| 2013/0165877 A1 | 6/2013 | Leeson et al. |
| 2013/0186405 A1 | 7/2013 | Krzyzanowski et al. |
| 2013/0190903 A1 | 7/2013 | Balakrishnan et al. |
| 2013/0191513 A1 | 7/2013 | Kamen et al. |
| 2013/0196703 A1 | 8/2013 | Masoud et al. |
| 2013/0204106 A1 | 8/2013 | Bennett |
| 2013/0204210 A1 | 8/2013 | Pratt et al. |
| 2013/0211206 A1 | 8/2013 | Sands et al. |
| 2013/0211854 A1 | 8/2013 | Wagstaff |
| 2013/0212168 A1 | 8/2013 | Bonasera et al. |
| 2013/0214925 A1 | 8/2013 | Weiss |
| 2013/0218053 A1 | 8/2013 | Kaiser et al. |
| 2013/0223979 A1 | 8/2013 | Locke et al. |
| 2013/0226607 A1 | 8/2013 | Woody et al. |
| 2013/0227128 A1 | 8/2013 | Wagstaff |
| 2013/0231596 A1 | 9/2013 | Hornbach et al. |
| 2013/0245387 A1 | 9/2013 | Patel |
| 2013/0253952 A1 | 9/2013 | Burke et al. |
| 2013/0255681 A1 | 10/2013 | Batch et al. |
| 2013/0267918 A1 | 10/2013 | Pan et al. |
| 2013/0267919 A1 | 10/2013 | Caso et al. |
| 2013/0268283 A1 | 10/2013 | Vann et al. |
| 2013/0271556 A1 | 10/2013 | Ross et al. |
| 2013/0282395 A1 | 10/2013 | Rustgi et al. |
| 2013/0285837 A1 | 10/2013 | Uchida |
| 2013/0297350 A1 | 11/2013 | Gross et al. |
| 2013/0304489 A1 | 11/2013 | Miller |
| 2013/0310726 A1 | 11/2013 | Miller et al. |
| 2013/0310778 A1 | 11/2013 | Locke et al. |
| 2013/0317753 A1 | 11/2013 | Kamen et al. |
| 2013/0325508 A1 | 12/2013 | Johnson et al. |
| 2013/0331748 A1 | 12/2013 | Wright et al. |
| 2013/0332197 A1 | 12/2013 | Hinkel |
| 2013/0335233 A1 | 12/2013 | Kamar et al. |
| 2013/0345524 A1 | 12/2013 | Meyer et al. |

(56) References Cited

U.S. PATENT DOCUMENTS

| | | |
|---|---|---|
| 2014/0002234 A1 | 1/2014 | Alwan |
| 2014/0028464 A1 | 1/2014 | Garibaldi |
| 2014/0031884 A1 | 1/2014 | Elghazzawi |
| 2014/0032231 A1 | 1/2014 | Semen et al. |
| 2014/0058344 A1* | 2/2014 | Toth ................. A61B 5/412 |
| | | 604/319 |
| 2014/0058714 A1 | 2/2014 | Boyer |
| 2014/0087762 A1 | 3/2014 | Galvin et al. |
| 2014/0100516 A1 | 4/2014 | Hunt et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0114236 A1 | 4/2014 | Gordon |
| 2014/0114237 A1 | 4/2014 | Gordon |
| 2014/0129250 A1 | 5/2014 | Daniel et al. |
| 2014/0148138 A1 | 5/2014 | Chou |
| 2014/0163490 A1 | 6/2014 | Locke et al. |
| 2014/0171753 A1 | 6/2014 | Montejo et al. |
| 2014/0187888 A1 | 7/2014 | Hatziantoniou |
| 2014/0194835 A1 | 7/2014 | Ehlert |
| 2014/0207090 A1 | 7/2014 | Jian |
| 2014/0222446 A1 | 8/2014 | Ash et al. |
| 2014/0235975 A1 | 8/2014 | Carnes |
| 2014/0244285 A1 | 8/2014 | Hinkle et al. |
| 2014/0244301 A1 | 8/2014 | Lee et al. |
| 2014/0244307 A1 | 8/2014 | Shutko et al. |
| 2014/0266713 A1 | 9/2014 | Sehgal et al. |
| 2014/0275876 A1 | 9/2014 | Hansen et al. |
| 2014/0278502 A1 | 9/2014 | Laskin |
| 2014/0280882 A1 | 9/2014 | Lacerte et al. |
| 2014/0297299 A1 | 10/2014 | Lester, IV |
| 2014/0303551 A1 | 10/2014 | Germain et al. |
| 2014/0316819 A1 | 10/2014 | Dunsirn et al. |
| 2014/0323906 A1 | 10/2014 | Peatfield et al. |
| 2014/0350966 A1 | 11/2014 | Khatana et al. |
| 2014/0366878 A1 | 12/2014 | Baron |
| 2014/0372147 A1 | 12/2014 | White |
| 2014/0372522 A1 | 12/2014 | Orona et al. |
| 2014/0375470 A1 | 12/2014 | Malveaux |
| 2014/0378895 A1 | 12/2014 | Barack |
| 2015/0012290 A1 | 1/2015 | Inciardi et al. |
| 2015/0019237 A1 | 1/2015 | Doyle et al. |
| 2015/0019257 A1 | 1/2015 | Doyle et al. |
| 2015/0046137 A1 | 2/2015 | Zeilinger |
| 2015/0066531 A1 | 3/2015 | Jacobson et al. |
| 2015/0072613 A1 | 3/2015 | Swanson |
| 2015/0094673 A1 | 4/2015 | Pratt et al. |
| 2015/0094674 A1 | 4/2015 | Pratt et al. |
| 2015/0094830 A1 | 4/2015 | Lipoma et al. |
| 2015/0095056 A1 | 4/2015 | Ryan et al. |
| 2015/0095059 A1 | 4/2015 | Yegge et al. |
| 2015/0095066 A1 | 4/2015 | Ryan et al. |
| 2015/0095068 A1 | 4/2015 | Ryan et al. |
| 2015/0100340 A1 | 4/2015 | Folsom et al. |
| 2015/0112707 A1 | 4/2015 | Manice et al. |
| 2015/0118662 A1 | 4/2015 | Ellison et al. |
| 2015/0119652 A1 | 4/2015 | Hyde et al. |
| 2015/0120318 A1 | 4/2015 | Toyama |
| 2015/0133829 A1 | 5/2015 | DeBusk et al. |
| 2015/0143300 A1 | 5/2015 | Zhang et al. |
| 2015/0164323 A1 | 6/2015 | Holtzclaw |
| 2015/0164376 A1 | 6/2015 | Huang |
| 2015/0186615 A1 | 7/2015 | Armor et al. |
| 2015/0189001 A1 | 7/2015 | Lee et al. |
| 2015/0227716 A1 | 8/2015 | Ryan et al. |
| 2015/0227717 A1 | 8/2015 | Ryan et al. |
| 2015/0231350 A1 | 8/2015 | Baloa Welzien et al. |
| 2015/0234557 A1 | 8/2015 | Dorn |
| 2015/0234995 A1 | 8/2015 | Casady et al. |
| 2015/0242578 A1 | 8/2015 | Siemon |
| 2015/0242583 A1 | 8/2015 | Edson |
| 2015/0254403 A1 | 9/2015 | Laperna |
| 2015/0257643 A1 | 9/2015 | Watson et al. |
| 2015/0261920 A1 | 9/2015 | Blick |
| 2015/0269323 A1 | 9/2015 | Ginsburg |
| 2015/0286970 A1 | 10/2015 | Dickerson et al. |
| 2015/0290364 A1 | 10/2015 | Wall et al. |
| 2015/0304478 A1 | 10/2015 | Kim et al. |
| 2015/0310182 A1 | 10/2015 | Henze et al. |
| 2015/0314083 A1* | 11/2015 | Blumberg, Jr. ....... A61M 5/142 |
| | | 604/500 |
| 2015/0324943 A1 | 11/2015 | Han et al. |
| 2015/0339445 A1 | 11/2015 | Gruby et al. |
| 2015/0363058 A1 | 12/2015 | Chung et al. |
| 2015/0370984 A1 | 12/2015 | Russell et al. |
| 2015/0370997 A1 | 12/2015 | Krongrad et al. |
| 2015/0379441 A1 | 12/2015 | Syed et al. |
| 2016/0004824 A1 | 1/2016 | Stanton et al. |
| 2016/0018963 A1 | 1/2016 | Robbins et al. |
| 2016/0042154 A1 | 2/2016 | Goldberg et al. |
| 2016/0044141 A1 | 2/2016 | Pfutzenreuter et al. |
| 2016/0055310 A1 | 2/2016 | Bentley et al. |
| 2016/0058286 A1 | 3/2016 | Joshua et al. |
| 2016/0063210 A1 | 3/2016 | Bardi et al. |
| 2016/0066864 A1 | 3/2016 | Frieder et al. |
| 2016/0080365 A1 | 3/2016 | Baker et al. |
| 2016/0085415 A1 | 3/2016 | Humphrys et al. |
| 2016/0098524 A1 | 4/2016 | Himmelstein |
| 2016/0110507 A1 | 4/2016 | Abbo |
| 2016/0128571 A1 | 5/2016 | Adler |
| 2016/0129186 A1 | 5/2016 | Douglas et al. |
| 2016/0135752 A1 | 5/2016 | Beaumont |
| 2016/0142443 A1 | 5/2016 | Ting et al. |
| 2016/0151015 A1 | 6/2016 | Condurso et al. |
| 2016/0154936 A1 | 6/2016 | Kalathil |
| 2016/0154943 A1 | 6/2016 | Cho et al. |
| 2016/0171866 A1 | 6/2016 | Dupasquier et al. |
| 2016/0180031 A1 | 6/2016 | Slater |
| 2016/0184496 A1 | 6/2016 | Jaecklein et al. |
| 2016/0184497 A1 | 6/2016 | Phillips et al. |
| 2016/0196399 A1 | 7/2016 | Bonhomme |
| 2016/0203275 A1 | 7/2016 | Benjamin et al. |
| 2016/0203283 A1 | 7/2016 | Baruah et al. |
| 2016/0209837 A1 | 7/2016 | Kim |
| 2016/0212577 A1 | 7/2016 | Dor et al. |
| 2016/0217433 A1 | 7/2016 | Walton et al. |
| 2016/0246943 A1 | 8/2016 | Lake et al. |
| 2016/0260035 A1 | 9/2016 | Crooks et al. |
| 2016/0287189 A1 | 10/2016 | Modai et al. |
| 2016/0308969 A1 | 10/2016 | Aihara et al. |
| 2016/0321404 A1 | 11/2016 | Ginsburg |
| 2016/0321422 A1 | 11/2016 | Albright |
| 2017/0004106 A1 | 1/2017 | Joshua et al. |
| 2017/0007494 A1 | 1/2017 | Rock et al. |
| 2017/0007748 A1 | 1/2017 | Locke et al. |
| 2017/0014028 A1 | 1/2017 | Clear, Jr. |
| 2017/0017765 A1 | 1/2017 | Yegge et al. |
| 2017/0032648 A1 | 2/2017 | Mcclain et al. |
| 2017/0046503 A1 | 2/2017 | Cho et al. |
| 2017/0053073 A1 | 2/2017 | Allen et al. |
| 2017/0055205 A1 | 2/2017 | Morris et al. |
| 2017/0065751 A1 | 3/2017 | Toth |
| 2017/0068781 A1 | 3/2017 | Zasowski et al. |
| 2017/0074717 A1 | 3/2017 | Pilkington et al. |
| 2017/0078396 A1 | 3/2017 | Haas et al. |
| 2017/0116373 A1 | 4/2017 | Ginsburg et al. |
| 2017/0140120 A1 | 5/2017 | Thrower |
| 2017/0150939 A1 | 6/2017 | Shah |
| 2017/0193181 A1 | 7/2017 | Carter et al. |
| 2017/0212995 A1 | 7/2017 | Ingmanson |
| 2017/0220755 A1 | 8/2017 | Fowler et al. |
| 2017/0257682 A1 | 9/2017 | Shtalryd |
| 2017/0270533 A1 | 9/2017 | Barton et al. |
| 2017/0273116 A1 | 9/2017 | Elghazzawi |
| 2017/0327371 A1 | 11/2017 | Bai et al. |
| 2017/0372010 A1 | 12/2017 | Doherty et al. |
| 2018/0004908 A1 | 1/2018 | Barrus et al. |
| 2018/0052454 A1 | 2/2018 | Magno et al. |
| 2018/0121629 A1 | 5/2018 | Dyer et al. |
| 2018/0139572 A1 | 5/2018 | Hansen |
| 2018/0144817 A1 | 5/2018 | Lofgren et al. |
| 2018/0158545 A1 | 6/2018 | Blomquist |
| 2018/0181714 A1 | 6/2018 | Pillarisetty et al. |
| 2018/0233016 A1 | 8/2018 | Daniel et al. |

(56)　　　　　　References Cited

U.S. PATENT DOCUMENTS

| | | | |
|---|---|---|---|
| 2018/0233221 A1 | 8/2018 | Blomquist |
| 2018/0279880 A1 | 10/2018 | Bacchi |
| 2018/0286502 A1 | 10/2018 | Lane et al. |
| 2018/0308569 A1 | 10/2018 | Luellen |
| 2018/0308573 A1 | 10/2018 | Hochrein et al. |
| 2018/0315492 A1 | 11/2018 | Bishop et al. |
| 2018/0322944 A1 | 11/2018 | Valdizan |

FOREIGN PATENT DOCUMENTS

| | | | |
|---|---|---|---|
| DE | 102010036405 A1 | 1/2012 |
| EP | 0980227 A1 | 2/2000 |
| EP | 0566381 B1 | 7/2002 |
| EP | 1231965 A2 | 8/2002 |
| EP | 1291802 A2 | 3/2003 |
| EP | 1309960 A1 | 5/2003 |
| EP | 0814864 B1 | 12/2003 |
| EP | 1407624 A2 | 4/2004 |
| EP | 1011420 B1 | 12/2004 |
| EP | 1495713 A1 | 1/2005 |
| EP | 1524619 A2 | 4/2005 |
| EP | 1540557 A2 | 6/2005 |
| EP | 1579367 A2 | 9/2005 |
| EP | 1587017 A2 | 10/2005 |
| EP | 1684146 A2 | 7/2006 |
| EP | 1788503 A2 | 5/2007 |
| EP | 1839244 A1 | 10/2007 |
| EP | 1839615 A1 | 10/2007 |
| EP | 1857950 A2 | 11/2007 |
| EP | 1870068 A1 | 12/2007 |
| EP | 1904964 A1 | 4/2008 |
| EP | 1934852 A1 | 6/2008 |
| EP | 1975828 A2 | 10/2008 |
| EP | 1993435 A2 | 11/2008 |
| EP | 2038786 A2 | 3/2009 |
| EP | 2040604 A2 | 4/2009 |
| EP | 2092470 A2 | 8/2009 |
| EP | 2146297 A1 | 1/2010 |
| EP | 2172859 A1 | 4/2010 |
| EP | 2214552 A1 | 8/2010 |
| EP | 2218478 A1 | 8/2010 |
| EP | 1404213 B1 | 3/2011 |
| EP | 1247229 B1 | 4/2011 |
| EP | 1406540 B1 | 6/2011 |
| EP | 1812094 B1 | 8/2011 |
| EP | 2384472 A1 | 11/2011 |
| EP | 2226002 B1 | 1/2012 |
| EP | 1610494 B1 | 3/2012 |
| EP | 1248660 B1 | 4/2012 |
| EP | 2023800 B1 | 4/2012 |
| EP | 2451513 A1 | 5/2012 |
| EP | 1248661 B1 | 8/2012 |
| EP | 2488977 A1 | 8/2012 |
| EP | 2562665 A2 | 2/2013 |
| EP | 2619723 A2 | 7/2013 |
| EP | 1881784 B1 | 10/2013 |
| EP | 2664194 A2 | 11/2013 |
| EP | 2743850 A2 | 6/2014 |
| EP | 2745204 A1 | 6/2014 |
| EP | 2795492 A1 | 10/2014 |
| EP | 2841895 A1 | 3/2015 |
| EP | 2850771 A1 | 3/2015 |
| EP | 2876567 A1 | 5/2015 |
| EP | 2891999 A2 | 7/2015 |
| EP | 2894581 A1 | 7/2015 |
| EP | 2906101 A2 | 8/2015 |
| EP | 2945084 A1 | 11/2015 |
| EP | 2962266 A1 | 1/2016 |
| EP | 2968829 A1 | 1/2016 |
| EP | 2973089 A1 | 1/2016 |
| EP | 3000082 A1 | 3/2016 |
| EP | 3010398 A1 | 4/2016 |
| EP | 3054389 A2 | 8/2016 |
| EP | 3070628 A1 | 9/2016 |
| EP | 3078010 A1 | 10/2016 |
| EP | 3096113 A1 | 11/2016 |
| EP | 2563437 B1 | 3/2017 |
| EP | 3134854 A1 | 3/2017 |
| EP | 3027242 B1 | 4/2017 |
| EP | 2556650 B1 | 5/2017 |
| EP | 3174569 A1 | 6/2017 |
| EP | 2632407 B1 | 8/2017 |
| EP | 3209358 A1 | 8/2017 |
| EP | 3041571 B1 | 9/2017 |
| EP | 2856767 B1 | 11/2017 |
| EP | 3252635 A1 | 12/2017 |
| EP | 2320971 B1 | 5/2018 |
| EP | 2335173 B1 | 5/2018 |
| EP | 3100188 B1 | 6/2018 |
| EP | 3330973 A1 | 6/2018 |
| EP | 3352174 A1 | 7/2018 |
| EP | 2440112 B1 | 10/2018 |
| EP | 3400549 A1 | 11/2018 |
| EP | 2992500 B1 | 12/2018 |
| EP | 2597584 B1 | 1/2019 |
| EP | 3219340 B1 | 1/2019 |
| EP | 2890456 B1 | 2/2019 |
| EP | 2881875 B1 | 5/2019 |
| EP | 2836269 B1 | 8/2019 |
| EP | 2866851 B1 | 9/2019 |
| GB | 2235877 A | 3/1991 |
| GB | 2409951 A | 7/2005 |
| GB | 2436160 A | 9/2007 |
| GB | 2449400 A | 11/2008 |
| GB | 2456708 A | 7/2009 |
| GB | 2423178 B | 5/2010 |
| GB | 2475091 A | 5/2011 |
| GB | 2488904 A | 9/2012 |
| GB | 2446923 B | 5/2013 |
| GB | 2499986 A | 9/2013 |
| GB | 2501256 A | 10/2013 |
| GB | 2491946 B | 8/2014 |
| GB | 2499873 B | 5/2016 |
| GB | 2533910 A | 7/2016 |
| GB | 2541286 A | 2/2017 |
| GB | 2550576 B | 6/2018 |
| WO | WO-9619335 A1 | 6/1996 |
| WO | WO-9627163 A1 | 9/1996 |
| WO | WO-9744745 A1 | 11/1997 |
| WO | WO-9924927 A1 | 5/1999 |
| WO | WO-9963886 A1 | 12/1999 |
| WO | WO-0060522 A2 | 10/2000 |
| WO | WO-0114048 A1 | 3/2001 |
| WO | WO-0133457 A1 | 5/2001 |
| WO | WO-0181829 A1 | 11/2001 |
| WO | WO-0217075 A2 | 2/2002 |
| WO | WO-0233577 A1 | 4/2002 |
| WO | WO-02078594 A2 | 10/2002 |
| WO | WO-02101713 A1 | 12/2002 |
| WO | WO-03054668 A2 | 7/2003 |
| WO | WO-03101508 A2 | 12/2003 |
| WO | WO-2004057514 A2 | 7/2004 |
| WO | WO-2004074457 A2 | 9/2004 |
| WO | WO-2005022349 A2 | 3/2005 |
| WO | WO-2005031632 A2 | 4/2005 |
| WO | WO-2005036447 A2 | 4/2005 |
| WO | WO-2005045461 A1 | 5/2005 |
| WO | WO-2005053793 A1 | 6/2005 |
| WO | WO-2005057466 A2 | 6/2005 |
| WO | WO-2005083619 A2 | 9/2005 |
| WO | WO-2005101282 A2 | 10/2005 |
| WO | WO-2005109297 A2 | 11/2005 |
| WO | WO-2005120097 A2 | 12/2005 |
| WO | WO-2006021154 A1 | 3/2006 |
| WO | WO-2006066583 A1 | 6/2006 |
| WO | WO-2006066585 A2 | 6/2006 |
| WO | WO-2006071711 A2 | 7/2006 |
| WO | WO-2006099120 A2 | 9/2006 |
| WO | WO-2006108858 A1 | 10/2006 |
| WO | WO-2006111109 A1 | 10/2006 |
| WO | WO-2007027490 A2 | 3/2007 |
| WO | WO-2007035646 A2 | 3/2007 |
| WO | WO-2007127879 A2 | 11/2007 |
| WO | WO-2007133478 A2 | 11/2007 |

(56) References Cited

FOREIGN PATENT DOCUMENTS

| | | | |
|---|---|---|---|
| WO | WO-2007137869 A2 | 12/2007 | |
| WO | WO-2008010012 A2 | 1/2008 | |
| WO | WO-2008036344 A1 | 3/2008 | |
| WO | WO-2008036360 A2 | 3/2008 | |
| WO | WO-2008039223 A1 | 4/2008 | |
| WO | WO-2008039314 A2 | 4/2008 | |
| WO | WO-2008062382 A2 | 5/2008 | |
| WO | WO-2008116295 A1 | 10/2008 | |
| WO | WO-2008150633 A2 | 12/2008 | |
| WO | WO-2009047524 A2 | 4/2009 | |
| WO | WO-2009140669 A2 | 11/2009 | |
| WO | WO-2010017484 A2 | 2/2010 | |
| WO | WO-2010025166 A1 | 3/2010 | |
| WO | WO-2010025467 A1 | 3/2010 | |
| WO | WO-2010078558 A1 | 7/2010 | |
| WO | WO-2010085033 A2 | 7/2010 | |
| WO | WO-2010089368 A2 | 8/2010 | |
| WO | WO-2010132617 A2 | 11/2010 | |
| WO | WO-2010145780 A1 | 12/2010 | |
| WO | WO-2011005633 A2 | 1/2011 | |
| WO | WO-2011023384 A1 | 3/2011 | |
| WO | WO-2011039676 A2 | 4/2011 | |
| WO | WO-2011046860 A2 | 4/2011 | |
| WO | WO-2011047334 A1 | 4/2011 | |
| WO | WO-2011107972 A1 | 9/2011 | |
| WO | WO-2011123933 A1 | 10/2011 | |
| WO | WO-2011124388 A1 | 10/2011 | |
| WO | WO-2011137230 A1 | 11/2011 | |
| WO | WO-2012009869 A1 | 1/2012 | |
| WO | WO-2012027342 A1 | 3/2012 | |
| WO | WO-2012027912 A1 | 3/2012 | |
| WO | WO-2012027913 A1 | 3/2012 | |
| WO | WO-2012027914 A1 | 3/2012 | |
| WO | WO-2012027915 A1 | 3/2012 | |
| WO | WO-2012027916 A1 | 3/2012 | |
| WO | WO-2012051278 A1 | 4/2012 | |
| WO | WO-2012100624 A1 | 8/2012 | |
| WO | WO-2012127281 A1 | 9/2012 | |
| WO | WO-2013025815 A1 | 2/2013 | |
| WO | WO-2013026999 A1 | 2/2013 | |
| WO | WO-2013036853 A2 | 3/2013 | |
| WO | WO-2013054217 A1 | 4/2013 | |
| WO | WO-2013061887 A1 | 5/2013 | |
| WO | WO-2013063848 A1 | 5/2013 | |
| WO | WO-2013102855 A1 | 7/2013 | |
| WO | WO-2013109517 A1 | 7/2013 | |
| WO | WO-2013138182 A1 | 9/2013 | |
| WO | WO-2013141870 A1 | 9/2013 | |
| WO | WO-2013155193 A1 | 10/2013 | |
| WO | WO-2013175076 A1 | 11/2013 | |
| WO | WO-2014015215 A2 | 1/2014 | |
| WO | WO-2014018786 A2 | 1/2014 | |
| WO | WO-2014075494 A1 | 5/2014 | |
| WO | WO-2014089086 A1 | 6/2014 | |
| WO | WO-2014100036 A1 | 6/2014 | |
| WO | WO-2014100687 A2 | 6/2014 | |
| WO | WO-2014106056 A2 | 7/2014 | |
| WO | WO-2014123846 A1 | 8/2014 | |
| WO | WO-2014133822 A2 | 9/2014 | |
| WO | WO-2014141221 A2 | 9/2014 | |
| WO | WO-2014145496 A1 | 9/2014 | |
| WO | WO-2014150255 A2 | 9/2014 | |
| WO | WO-2014152963 A1 | 9/2014 | |
| WO | WO-2014189070 A1 | 11/2014 | |
| WO | WO-2014009876 A3 | 12/2014 | |
| WO | WO-2015019273 A2 | 2/2015 | |
| WO | WO-2015025482 A1 | 2/2015 | |
| WO | WO-2015026387 A1 | 2/2015 | |
| WO | WO-2015050816 A1 | 4/2015 | |
| WO | WO-2015078112 A1 | 6/2015 | |
| WO | WO-2015085249 A1 | 6/2015 | |
| WO | WO-2015091070 A1 | 6/2015 | |
| WO | WO-2015124670 A1 | 8/2015 | |
| WO | WO-2015132528 A1 | 9/2015 | |
| WO | WO-2015137126 A1 | 9/2015 | |
| WO | WO-2015140801 A2 | 9/2015 | |
| WO | WO-2015143099 A2 | 9/2015 | |
| WO | WO-2015145455 A1 | 10/2015 | |
| WO | WO-2015156143 A1 | 10/2015 | |
| WO | WO-2015164787 A1 | 10/2015 | |
| WO | WO-2015179915 A1 | 12/2015 | |
| WO | WO-2015179916 A1 | 12/2015 | |
| WO | WO-2015179917 A1 | 12/2015 | |
| WO | WO-2015181836 A2 | 12/2015 | |
| WO | WO-2015187480 A1 | 12/2015 | |
| WO | WO-2016001088 A1 | 1/2016 | |
| WO | WO-2016006536 A1 | 1/2016 | |
| WO | WO-2016033496 A1 * | 3/2016 | ........ A61M 5/31571 |
| WO | WO-2016061146 A1 * | 4/2016 | ............ G16H 10/60 |
| WO | WO-2016075656 A1 | 5/2016 | |
| WO | WO-2016108163 A1 | 7/2016 | |
| WO | WO-2016118318 A1 | 7/2016 | |
| WO | WO-2016120820 A2 | 8/2016 | |
| WO | WO-2016136694 A1 | 9/2016 | |
| WO | WO-2016141799 A1 | 9/2016 | |
| WO | WO-2016151364 A1 | 9/2016 | |
| WO | WO-2016160849 A1 | 10/2016 | |
| WO | WO-2016175649 A1 | 11/2016 | |
| WO | WO-2016178936 A1 | 11/2016 | |
| WO | WO-2016190978 A1 | 12/2016 | |
| WO | WO-2017001848 A1 | 1/2017 | |
| WO | WO-2017004423 A1 | 1/2017 | |
| WO | WO-2017027729 A2 | 2/2017 | |
| WO | WO-2017035024 A1 | 3/2017 | |
| WO | WO-2017053384 A1 | 3/2017 | |
| WO | WO-2017062042 A1 | 4/2017 | |
| WO | WO-2017087157 A1 | 5/2017 | |
| WO | WO-2017139686 A1 | 8/2017 | |
| WO | WO-2017142100 A1 | 8/2017 | |
| WO | WO-2017165895 A1 | 9/2017 | |
| WO | WO-2017192673 A1 | 11/2017 | |
| WO | WO-2017197357 A1 | 11/2017 | |
| WO | WO-2018007100 A1 | 1/2018 | |
| WO | WO-2018013666 A1 | 1/2018 | |
| WO | WO-2018033819 A1 | 2/2018 | |
| WO | WO-2018044894 A1 | 3/2018 | |
| WO | WO-2018064234 A1 | 4/2018 | |
| WO | WO-2018067593 A2 | 4/2018 | |
| WO | WO-2018082813 A1 | 5/2018 | |
| WO | WO-2018091492 A1 | 5/2018 | |
| WO | WO-2018096390 A1 | 5/2018 | |
| WO | WO-2018145880 A1 | 8/2018 | |
| WO | WO-2018148017 A1 | 8/2018 | |
| WO | WO-2018148487 A1 | 8/2018 | |

OTHER PUBLICATIONS

Hartmann Vivano., "Vivano—Product Application Description," retrieved from http://www.vivanosystem.info/20809.php, accessed on Feb. 28, 2013, 3 pages.

International Preliminary Report on Patentability for Application No. PCT/US2017/032545, mailed on Nov. 22, 2018, 15 pages.

International Search Report and Written Opinion for Application No. PCT/US2017/032545, mailed on Sep. 29, 2017, 19 pages.

Invitation to Pay Additional Fees and Partial Search Report for Application No. PCT/US2017/032545, mailed Jul. 28, 2017, 18 pages.

* cited by examiner

WOUND COUPLING DETECTION PROCESS

FLOW ESTIMATION PROCESS

AUTOMATIC WOUND COUPLING DETECTION IN NEGATIVE PRESSURE WOUND THERAPY SYSTEMS

CROSS-REFERENCE TO RELATED APPLICATIONS

This application is a divisional of U.S. application Ser. No. 16/300,449, filed Nov. 9, 2018, which is a national stage application of International Patent Application No. PCT/US2017/032545, filed May 12, 2017, which claims the benefit of U.S. Provisional Application No. 62/335,978, filed May 13, 2016, and U.S. Provisional Application No. 62/378,856, filed Aug. 24, 2016; the disclosures of which are hereby incorporated by reference in their entirety.

BACKGROUND

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

BRIEF DESCRIPTION OF THE DRAWINGS

Embodiments of the present disclosure will now be described hereinafter, by way of example only, with reference to the accompanying drawings in which.

SUMMARY

Figure 1:
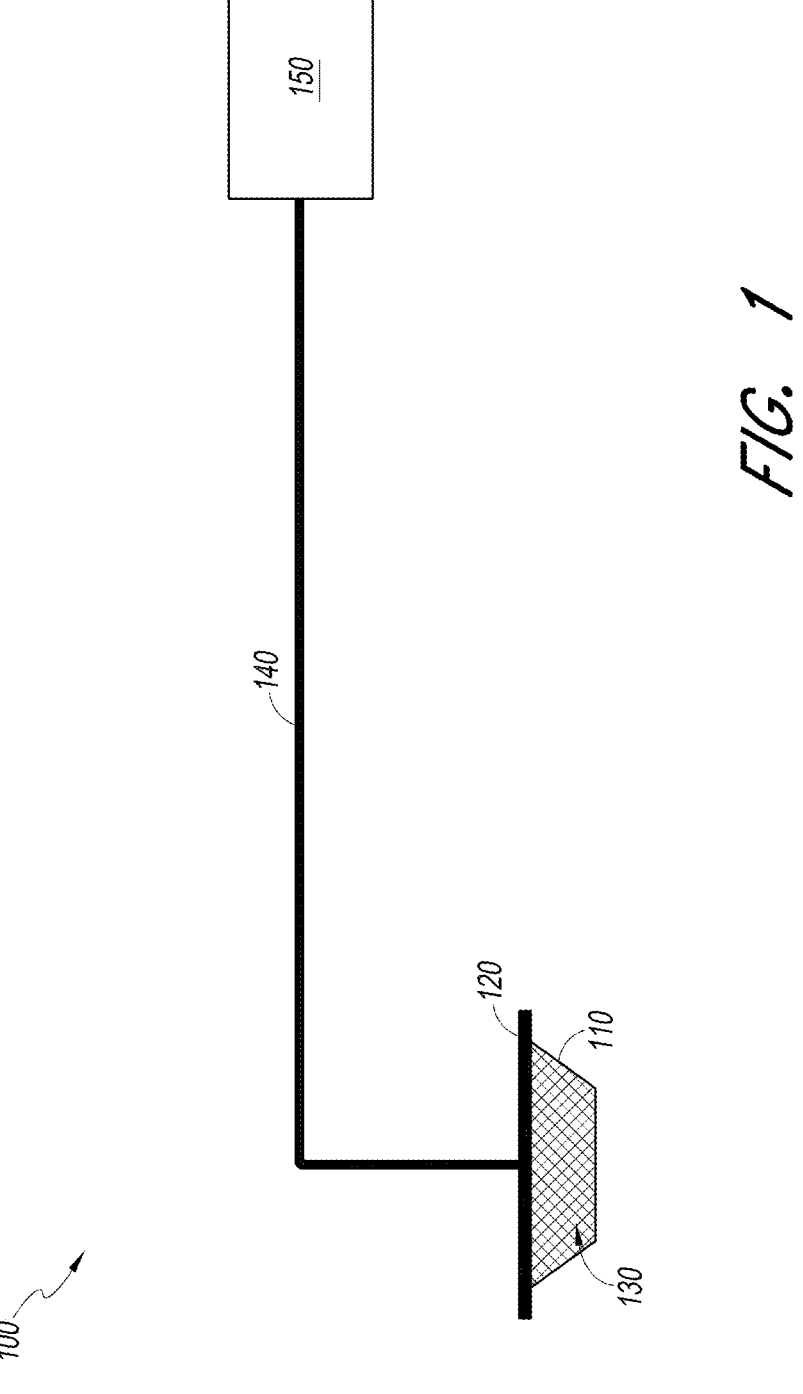
FIG. 1 illustrates a negative pressure wound therapy system according to some embodiments.

In some embodiments, an apparatus for applying negative pressure to a wound is disclosed. The apparatus can include: a negative pressure source configured to couple via a fluid flow path to a wound dressing and provide negative pressure to the wound dressing; a sensor configured to monitor pressure in the fluid flow path; and a controller configured to: determine that the wound dressing is coupled to a wound from a change in a magnitude of pressure in the fluid flow path over a time duration being indicative of a steady state condition while the negative pressure source maintains negative pressure in the fluid flow path within a target pressure range, output a first indication denoting that the wound dressing is coupled to the wound, determine that the wound dressing is not coupled to the wound from the change in the magnitude of pressure in the fluid flow path over the time duration being indicative of a chaotic condition while the negative pressure source maintains negative pressure in the fluid flow path within the target pressure range, and output a second indication different from the first indication denoting that the wound dressing is not coupled to the wound.

The apparatus of the preceding paragraph can include one or more of the following features: The controller is further configured to: in response to the determination that the wound dressing is coupled to the wound, store, in a memory device, device usage data indicating a compliant use of the negative pressure source. The controller is further configured to: in response to the determination that the wound dressing is not coupled to the wound, store, in a memory device, device usage data indicating a misuse use of the negative pressure source. The device usage data comprises one or more of a pressure level, an alarm, an exudate level, an event log, or a therapy duration. The controller is further configured to compare a measure of irregularity of the change in the magnitude over the time duration to a threshold to determine whether the change in the magnitude over the time duration is indicative of the steady state condition. The measure of irregularity is responsive to the change in the magnitude over the time duration of at least 1 second, 10 seconds, 30 seconds, 1 minute, or 5 minutes. The controller is further configured to: perform a statistical operation, a trending operation, a filtering operation, a cumulative summation operation, or a low-pass filtering operation on the magnitude over the time duration to generate an output value; and determine that the change in the magnitude over the time duration is indicative of the steady state condition in response to a determination that the output value is indicative of the steady state condition. The controller is configured to determine that the change in the magnitude over the time duration is indicative of the steady state condition from a time domain representation of the magnitude over the time duration and a frequency domain representation of the magnitude over the time duration. The controller is further configured to compare the magnitude over the time duration to a pressure pattern to determine whether the change in the magnitude over the time duration is indicative of the steady state condition. The pressure pattern is indicative of pressure in the fluid flow path when the wound dressing is coupled to the wound while the negative pressure source maintains negative pressure in the fluid flow path within the target pressure range. The pressure pattern is indicative of pressure in the fluid flow path when the wound dressing is not coupled to the wound while the negative pressure source maintains negative pressure in the fluid flow path within the target pressure range. The first indication denotes a compliant use of the negative pressure source, and the second indication denotes a non-compliant use of the negative pressure source. The controller is further configured to: output the first indication for storage in a memory device, or output the second indication for storage in the memory device. The controller is further configured to: output the first indication by causing a transmitter to transmit the first indication to a computing device via a communication network, or output the second indication by causing the transmitter to transmit the second indication to the computing device via the communication network. The controller is further configured to: output the first indication for presentation to a user, or output the second indication for presentation to the user. The fluid flow path comprises at least one lumen. The fluid flow path comprises a plurality of lumens. The controller is configured to activate and deactivate the negative pressure source responsive to the first indication or the second indication. The negative pressure source is configured to perform negative pressure therapy when the magnitude over the time duration is maintained within the target pressure range.

In some embodiments, a method of operating a negative pressure wound therapy apparatus is disclosed. The method can include: providing negative pressure to a wound dressing via a fluid flow path using a negative pressure source; monitoring with a sensor pressure in the fluid flow path; determining whether the wound dressing is coupled to a wound from a change in a magnitude of pressure in the fluid flow path over a time duration being indicative of a steady state condition while maintaining negative pressure in the fluid flow path within a target pressure range; in response to determining that the wound dressing is coupled to the wound from the change in the magnitude over the time duration, outputting a first indication denoting that the wound dressing is coupled to the wound; and in response to determining that the wound dressing is not coupled to the wound from the change in the magnitude over the time duration, outputting a second indication different from the first indication denoting that the wound dressing is not coupled to the wound.

The method of the preceding paragraph can include one or more of the following features: The method can further include storing, in a memory device, device usage data associated with a compliant use of the negative pressure wound therapy apparatus in response to determining the wound dressing is coupled to the wound. The method can further include storing, in a memory device, device usage data associated with a misuse use of the negative pressure wound therapy apparatus in response to determining the wound dressing is not coupled to the wound. The device usage data comprises one or more of a pressure level, an alarm, an exudate level, an event log, or a therapy duration. Said determining comprises comparing a measure of irregularity of the change in the magnitude over the time duration to a threshold. The measure of irregularity is responsive to the change in the magnitude over the time duration of at least 1 second, 10 seconds, 30 seconds, 1 minute, or 5 minutes. The method can further include performing a statistical operation, a trending operation, a filtering operation, a cumulative summation operation, or a low-pass filtering operation on the magnitude over time to generate an output value, wherein said determining comprises determining whether the change in the magnitude over the time duration is indicative of the steady state condition in response to determining that the output value is indicative of the steady state condition. The method can further include comparing the magnitude over the time duration to a pressure pattern to determine whether the change in the magnitude over the time duration is indicative of the steady state condition.

In some embodiments, an apparatus for applying negative pressure to a wound is disclosed. The apparatus comprising: a negative pressure source configured to couple via a fluid flow path to a wound dressing and provide negative pressure to the wound dressing; a sensor configured to monitor pressure in the fluid flow path; and a controller configured to: based at least in part on the pressure in the fluid flow path, determine that the wound dressing is coupled to a wound based on at least one of detection of change in flow of gas in the fluid flow path, detection of change in flow of exudate in the fluid flow path, change in vacuum level if the fluid flow path, or detection of presence of blood in the fluid flow path, and output an indication that the wound dressing is coupled to the wound.

The apparatus of the preceding paragraph can include one or more of the following features: The controller is configured to determine that the wound dressing is coupled to the wound further based on an activity level of the negative pressure source. The negative pressure source comprises a pump operated by an actuator, and wherein the activity level comprises at least one of a pump speed, a pulse width modulation (PWM) signal configured to drive the actuator, or a current signal configured to drive the actuator. The controller is configured to determine a first indicator associated with change in the activity level over a time duration. The first indicator comprises a statistical indicator. The controller is further configured to perform a time series analysis to determine if the first indicator deviates from a first threshold and in response to a determination that the first indicator deviates from the first threshold, determine that the wound dressing is coupled to the wound. The time series analysis comprises determination of a cumulative sum (Cusum) of the first indicator. The Cusum of the first indicators comprises a non-causal Cusum, sliding causal Cusum, or cumulative causal Cusum. The first indicator comprises kurtosis of standard deviation of the activity level, and wherein the first indicator is indicative of a change in flow of exudate in the fluid flow path. The controller is further configured to determine a cumulative sum (Cusum) of second indicator associated with change in the activity level over the time duration, the second indicator different from the first indicator. The second indicator comprises standard deviation of the activity level indicative of a change in a gas leak rate in the fluid flow path, and the controller is further configured to determine if the second indicator deviates from a second threshold and in response to a determination that the second indicator deviates from the second threshold, determine that the wound dressing is coupled to the wound. The controller is further configured to determine a cumulative sum (Cusum) of third indicator associated with change in the pressure in the fluid flow path over the time duration, the third indicator different from the first and second indicators. The third indicator comprises mean pressure in the fluid flow path indicative of a change in negative pressure in the fluid flow path, and the controller is further configured to determine if the third indicator deviates from a third threshold and in response to a determination that the third indicator deviates from the third threshold, determine that the wound dressing is coupled to the wound.

In some embodiments, a method for applying negative pressure to a wound is disclosed. The method can include: providing negative pressure with a negative pressure source to a wound dressing via a fluid flow path; monitoring pressure in the fluid flow path; and based at least in part on the pressure in the fluid flow path, determining that the wound dressing is coupled to a wound from one of detection of change in flow of gas in the fluid flow path, detection of change in flow of exudate in the fluid flow path, change in vacuum level if the fluid flow path, or detection of presence of blood in the fluid flow path; and outputting an indication that the wound dressing is coupled to the wound.

The method of the preceding paragraph can include one or more of the following features: Said determining comprises determining that the wound dressing is coupled to the wound further from an activity level of the negative pressure source. The negative pressure source comprises a pump operated by an actuator, and the activity level comprises at least one of a pump speed, a pulse width modulation (PWM) signal configured to drive the actuator, or a current signal configured to drive the actuator. The method can further include determining a first indicator associated with change in the activity level over a time duration. The first indicator comprises a statistical indicator. The method can further include performing a time series analysis to determine if the first indicator deviates from a first threshold and, in response to determining that the first indicator deviates from the first threshold, determining that the wound dressing is coupled to the wound. The time series analysis comprises determination of a cumulative sum (Cusum) of the first indicator. The Cusum of the first indicators comprises a non-causal Cusum, sliding causal Cusum, or cumulative causal Cusum. The first indicator comprises kurtosis of standard deviation of the activity level, and the first indicator is indicative of a change in flow of exudate in the fluid flow path. The method can further include determining a cumulative sum (Cusum) of second indicator associated with change in the activity level over the time duration, the second indicator different from the first indicator. The second indicator comprises standard deviation of the activity level indicative of a change in a gas leak rate in the fluid flow path, and the method can further include determining if the second indicator deviates from a second threshold and, in response to determining that the second indicator deviates from the second threshold, determining that the wound dressing is coupled to the wound. The method can further include determining a cumulative sum (Cusum) of third indicator associated with change in the pressure in the fluid flow path over the time duration, the third indicator different from the first and second indicators. The third indicator comprises mean pressure in the fluid flow path indicative of a change in negative pressure in the fluid flow path, and the method can further include determining if the third indicator deviates from a third threshold and, in response to determining that the third indicator deviates from the third threshold, determining that the wound dressing is coupled to the wound.

DETAILED DESCRIPTION

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

TNP therapy can assist in the closure and healing of many forms of "hard to heal" wounds by reducing tissue oedema, encouraging blood flow and granular tissue formation, or removing excess exudate and can reduce bacterial load (and thus infection risk). In addition, TNP therapy may allow for less disturbance of a wound leading to more rapid healing. TNP systems can also assist in the healing of surgically closed wounds by removing fluid or help to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as —X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of –X mmHg reflects pressure that is X mmHg below atmospheric pressure, such as a pressure of (760–X) mmHg. In addition, negative pressure that is "less" or "smaller" than –X mmHg corresponds to pressure that is closer to atmospheric pressure (e.g., –40 mmHg is less than –60 mmHg). Negative pressure that is "more" or "greater" than –X mmHg corresponds to pressure that is further from atmospheric pressure (e.g., –80 mmHg is more than –60 mmHg).

Overview

It may be difficult, in some instances, to confirm whether a negative pressure source, such as a pump, of a TNP apparatus (sometimes referred to herein as a pump assembly) is in use on a patient. A TNP apparatus can log the usage of its negative pressure source as a function of time between the activation and deactivation of the negative pressure source, as well as log events such as alarms, measured pressure, or changes to a therapy program administered by the TNP apparatus. However, the time between the activation and deactivation and the log events may not enable the TNP apparatus to confidently determine whether the negative pressure source is activated but not coupled via a fluid flow path to a wound. The TNP apparatus may, for instance, be unable to distinguish with confidence whether the negative pressure source is being used to treat a wound or instead being used while uncoupled from a wound and simply placed aside or in storage with the wound dressing not forming a substantially fluid tight seal over any surface or forming the seal over a surface other than tissue of the patient (for example, the dressing may be positioned over a table, door, etc.). Moreover, the TNP apparatus may be used for training, tampered with in a way that impacts treatment, or it may take a long time to set up use on a patient. As a result, it may be difficult to distinguish data collected from such uses or situations and data collected from treatment use on the patient.

In order to accurately understand the usage of a TNP apparatus, it can be desirable to know with greater confidence if a negative pressure source of the TNP apparatus is in use on a patient. For example, it may be desirable to monitor compliance of use of the TNP apparatus and thus to determine whether the TNP apparatus is being used in a complaint manner, such as to treat a wound, or instead being used in a non-compliant matter, such as being turned on but left unconnected to a wound.

Advantageously, in certain embodiments, a TNP apparatus can automatically detect whether a negative pressure source of TNP apparatus is coupled via a fluid flow path to a wound, such as the wound cavity 110. As a result, the TNP apparatus can automatically determine whether the TNP apparatus is in use on a patient and thus used in a compliant manner. This automatic determination by the TNP apparatus can moreover enable data collected by the TNP apparatus for diagnosis or compliance of the patient to be validated as resulting from therapeutic use on the patient.

In one implementation, a TNP apparatus can analyze a magnitude of pressure (such as by measuring raw peak-to-peak pressure readings) in a TNP system that includes the TNP apparatus to determine whether the negative pressure source is pumping on or against a wound dressing coupled to a wound, such as the wound cover 120 and the wound filler 130 coupled to the wound cavity 110, or against its own system (for example, the negative pressure source or the wound dressing may be left uncoupled or instead may be coupled to something other than a wound like an inanimate object). When the negative pressure source may be maintaining pressure against its own system rather than against the wound dressing coupled to the wound, the magnitude of pressure in the TNP system can relatively quickly begin to follow a regular pattern or reach a steady state condition because there may be no liquid moving through the TNP system and the TNP system may not be moving or flexing irregularly. The TNP apparatus can accordingly determine whether the change in the magnitude of pressure in the TNP system follows an irregular pattern or a chaotic condition indicative of use of the TNP apparatus on a patient or a regular pattern or a steady state condition not indicative of use of the TNP apparatus on a patient.

Moreover, a TNP apparatus can analyze artifacts in a pressure signal to determine whether the negative pressure source is pumping against a wound dressing coupled to a wound. The artifacts can be produced by mechanical or fluidic changes in a TNP system that includes the TNP apparatus. For example, mechanical movement at a wound (for example, due to patient's movement) coupled to a wound dressing can manifest as an artifact in the pressure signal. As another example, liquid passage in the TNP system can manifest as an artifact in the pressure signal. Notably, some artifacts may appear to be random while other artifacts, such as from pulse or respiration, may follow a substantially periodic pattern.

Negative Pressure System

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renays Soft Port available from Smith & Nephew. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapor permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys Aft and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Figure 2A:
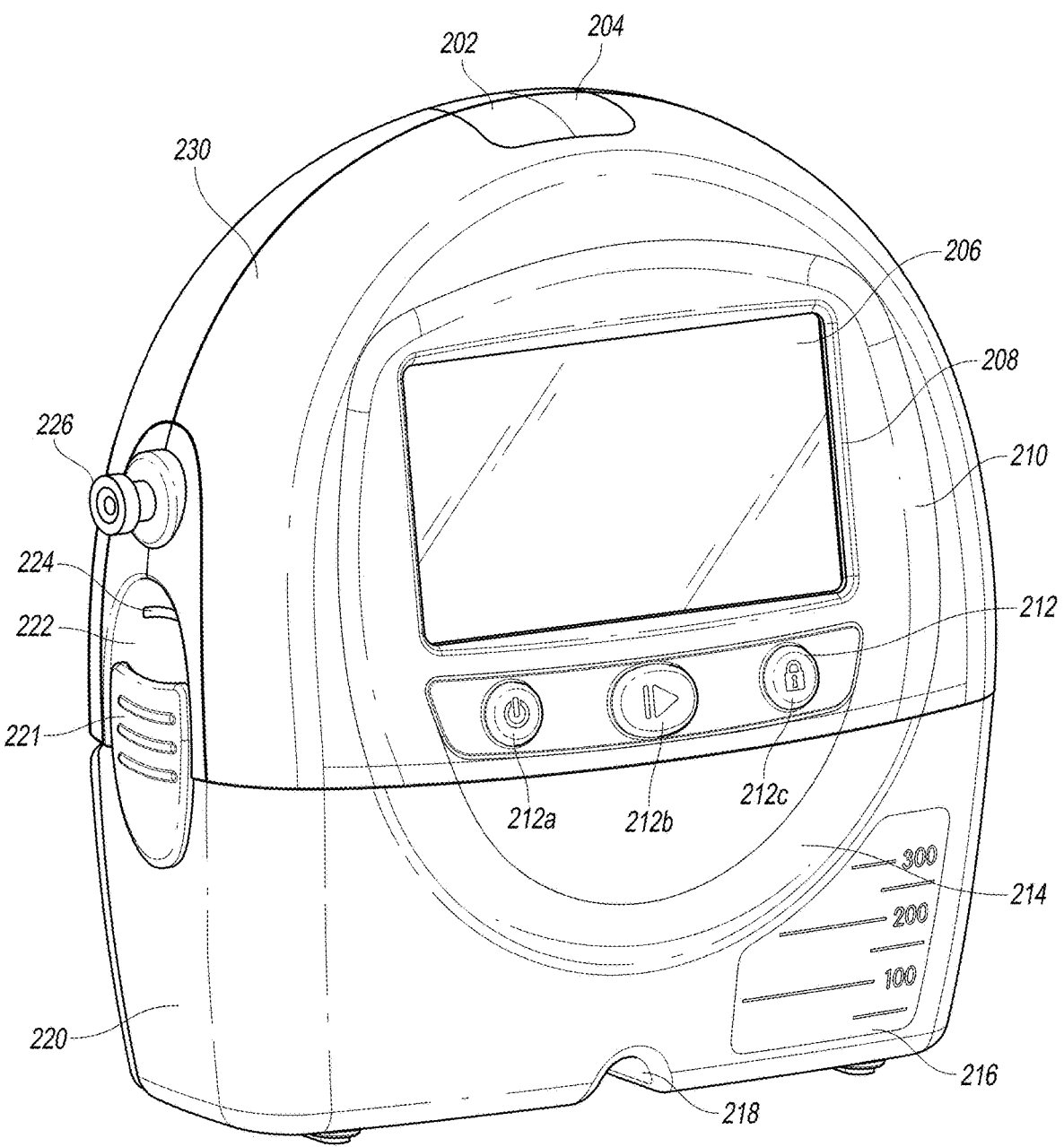
FIGS. 2A, 2B, and 2C illustrate a pump assembly and canister according to some embodiments.

FIG. 2A illustrates a front view of a pump assembly 230 and canister 220 according to some embodiments. As is illustrated, the pump assembly 230 and the canister are connected, thereby forming a negative pressure wound therapy device. The pump assembly 230 can be similar to or the same as the pump assembly 150 in some embodiments.

The pump assembly 230 includes one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can comprise additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons configured to allow the user to operate and monitor the operation of the TNP system. As is illustrated, there buttons 212a, 212b, and 212c (collectively referred to as buttons 212) are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 comprises a tubing channel 218 for connecting to the conduit 140. In some embodiments, various of these features, such as the gripping portion 214, are omitted or various additional features are added to the canister 220. Any of the disclosed canisters may include or may omit a solidifier.

Figure 2B:
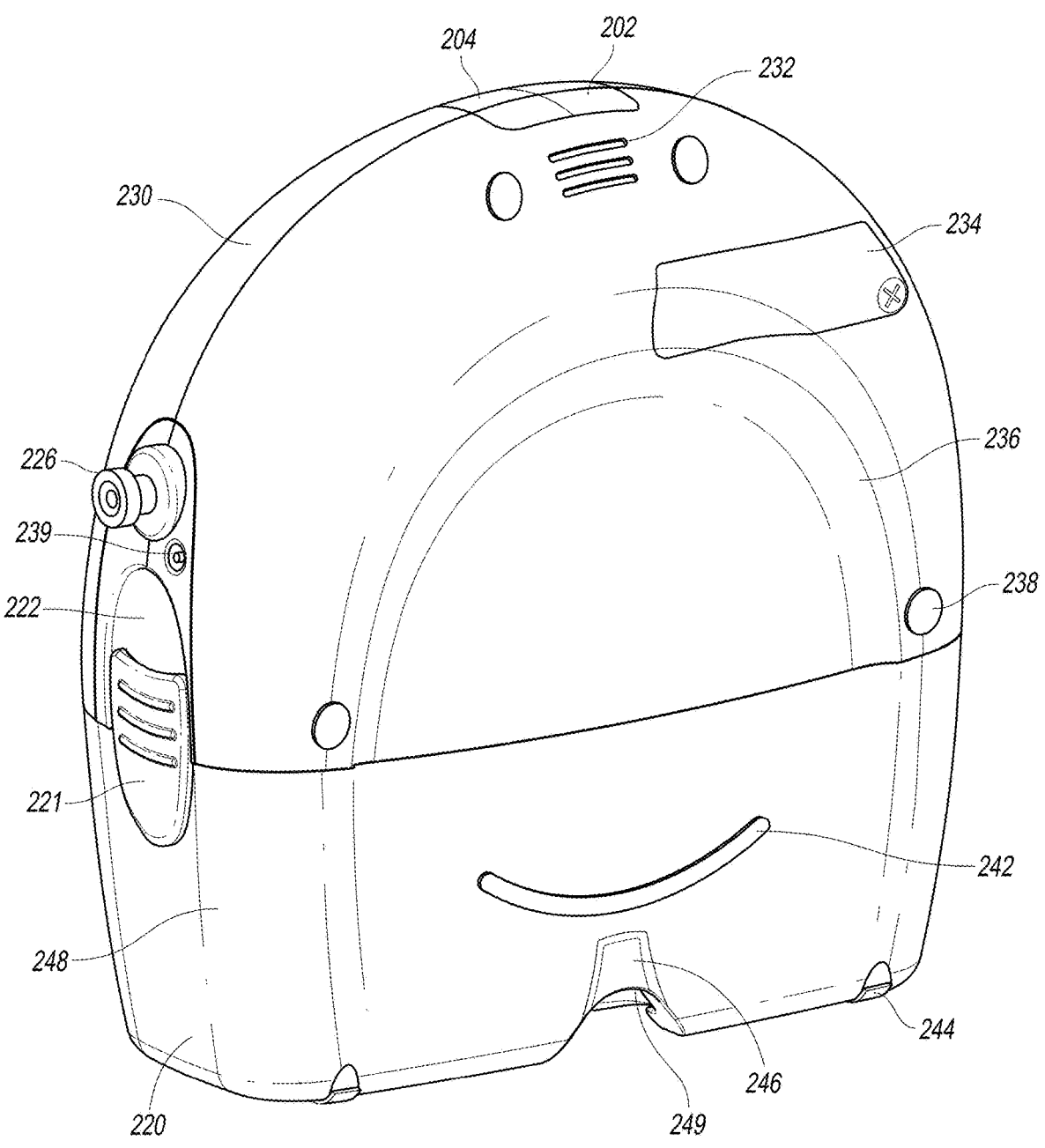

FIG. 2B illustrates a rear view of the pump assembly 230 and canister 220 according to some embodiments. The pump assembly 230 comprises a speaker port 232 for producing sound. The pump assembly 230 includes a filter access door 234 with a screw for removing the access door 234, accessing, and replacing one or more filters, such as antibacterial or odor filters. The pump assembly 230 comprises a gripping portion 236 formed in the case of the pump assembly. The gripping portion 236 can be configured to allow the user to hold the pump assembly 230, such as during removal of the canister 220. The pump assembly 230 includes one or more covers 238 configured to as screw covers or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some embodiments, the pump assembly can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
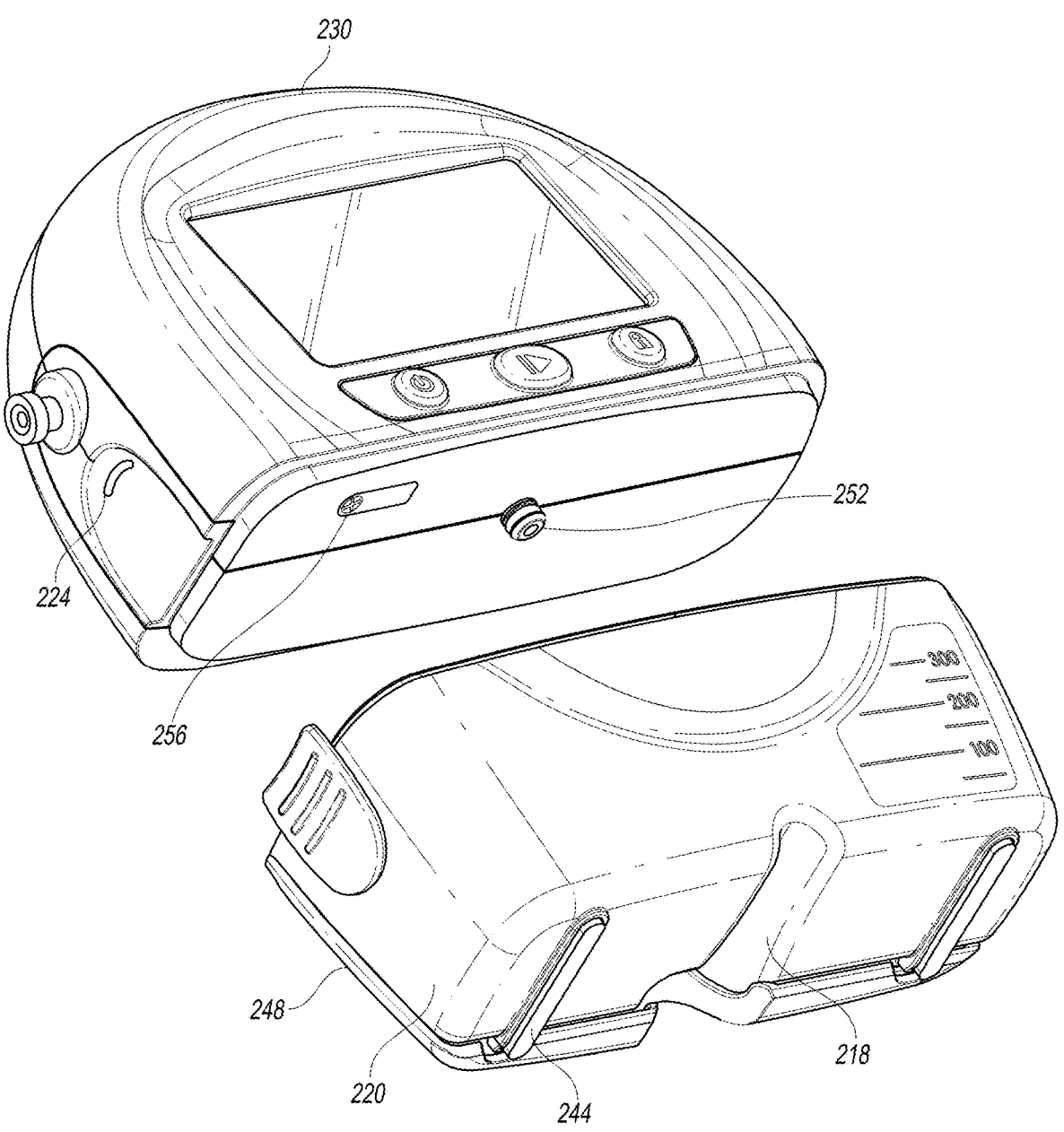

FIG. 2C illustrates a view of the pump assembly 230 separated from the canister 220 according to some embodiments. The pump assembly 230 includes a vacuum attachment, connector, or inlet 252 through which a vacuum pump communicates negative pressure to the canister 220. The pump assembly aspirates fluid, such as gas, from the wound via the inlet 252. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, or hybrid data transfer interfaces, such as SD, Compact Disc (CD), DVD, FireWire, Thunderbolt, PCI Express, and the like. In other embodiments, one or more of these additional ports are accessed through the door 234.

Figure 3A:
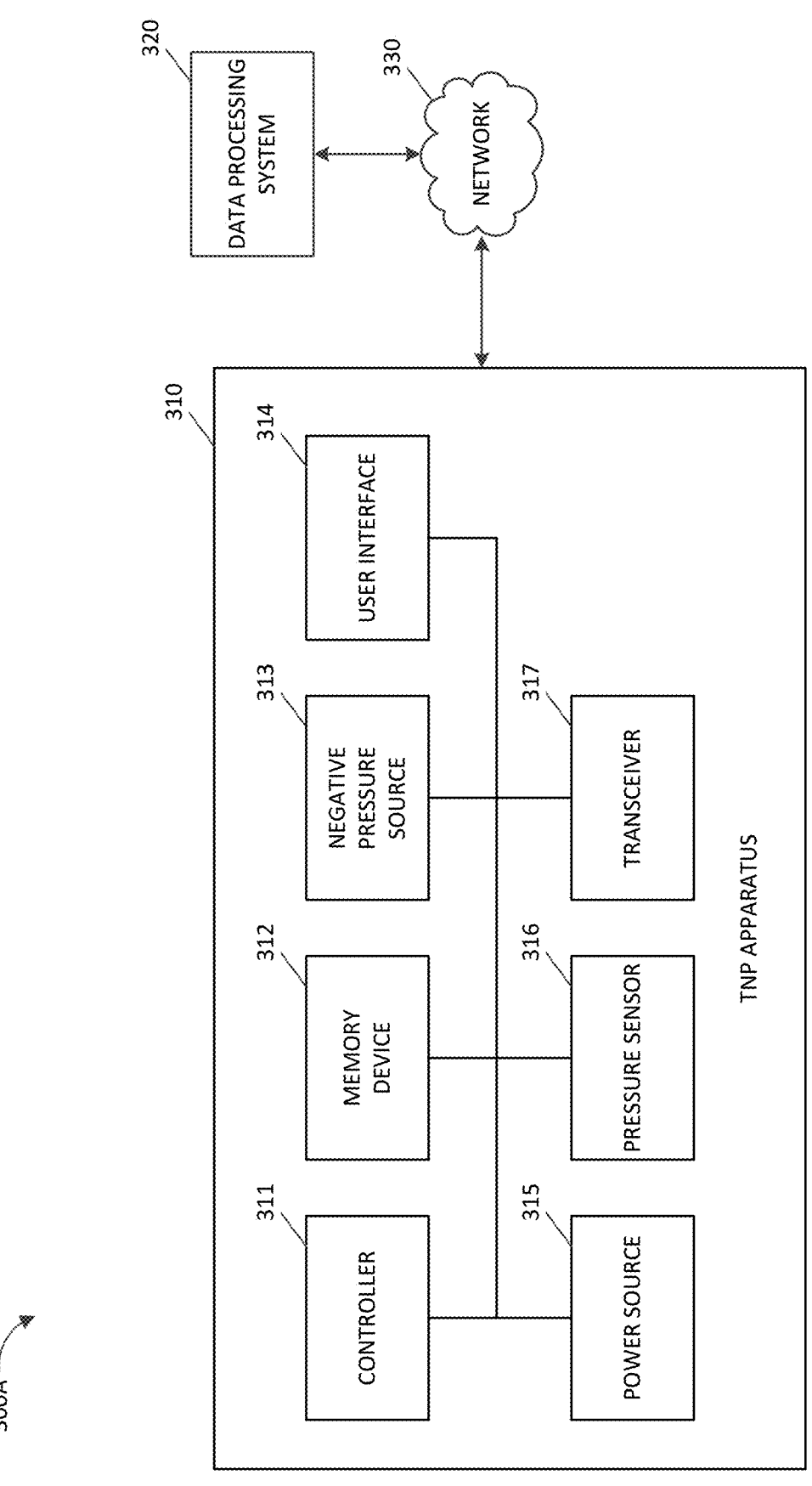
FIGS. 3A, 3B, 3C, 3D, 3E, 3F, and 3G illustrate components of a negative pressure therapy system according to some embodiments.

FIG. 3A illustrates components of a negative pressure therapy system 300A that includes a TNP apparatus 310 and a remote data processing system 320. The TNP apparatus 310 can be used to treat a wound using a wound dressing that is in fluidic communication with the TNP apparatus 310 via a fluid flow path. The TNP apparatus 310 can include a controller 311, a memory device 312, a negative pressure source 313, a user interface 314, a power source 315, a pressure sensor 316, and a transceiver 317 that are configured to electrically communicate with one another. The power source 315 can provide power to one or more components of the TNP apparatus 310. The TNP apparatus 310 can operate at the pressure levels and using control approaches as described herein or similar to those described in U.S. Patent Publication Nos. 2016/0136339 and 2016/0184496, which are incorporated by reference in their entirety. The TNP apparatus 310 can be similar to or the same as the pump assembly 150 in some embodiments.

The controller 311 can control operations of one or more other components of the TNP apparatus 310 according at least to instructions stored in the memory device 312. The controller 311 can, for instance, control operations of and supply of negative pressure by the negative pressure source 313. The negative pressure source 313 can include a pump, such as, without limitation, a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, or any other suitable pump or micropump or any combinations of the foregoing.

The user interface 314 can include one or more elements that receive user inputs or provide user outputs to a patient or caregiver. The one or more elements that receive user inputs can include buttons, switches, dials, touch screens, or the like. The user interface 314 can, for example, be used to generate and display a report or other information reflecting data from therapy use, data from non-compliant use, or a comparison of data from therapy use versus non-compliant use. As another example, the user interface 314 may receive a user input providing a patient reference number or another unique identifier, and the TNP apparatus 310 may then be activated for use by the patient and data collected and stored as described herein may be associated with the patient reference number for usage monitoring for a particular patient.

Figure 3B:
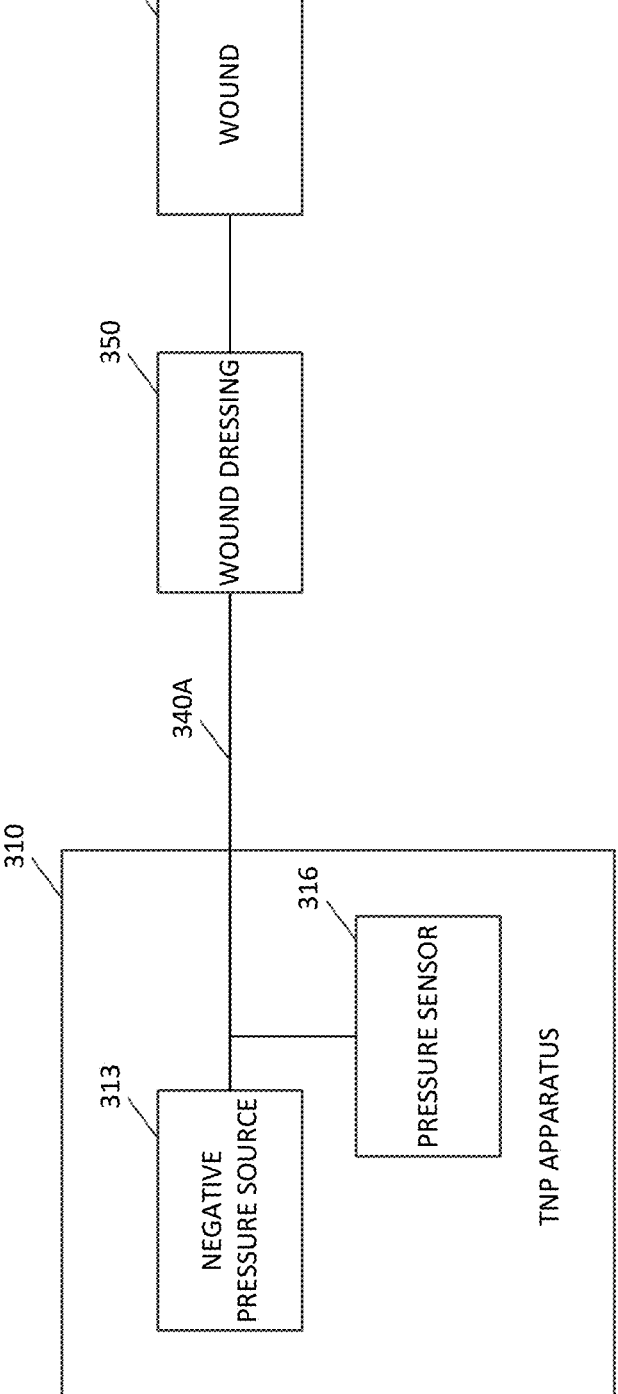
Figure 3C:
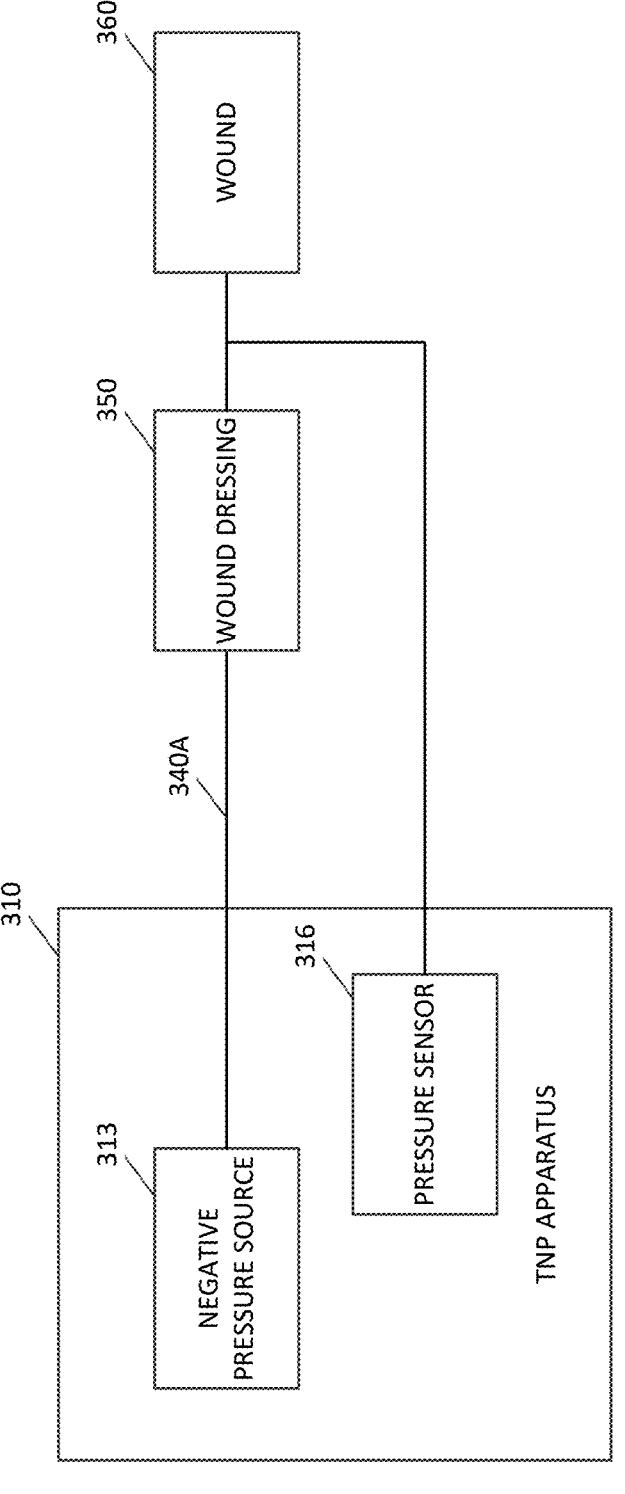
Figure 3D:
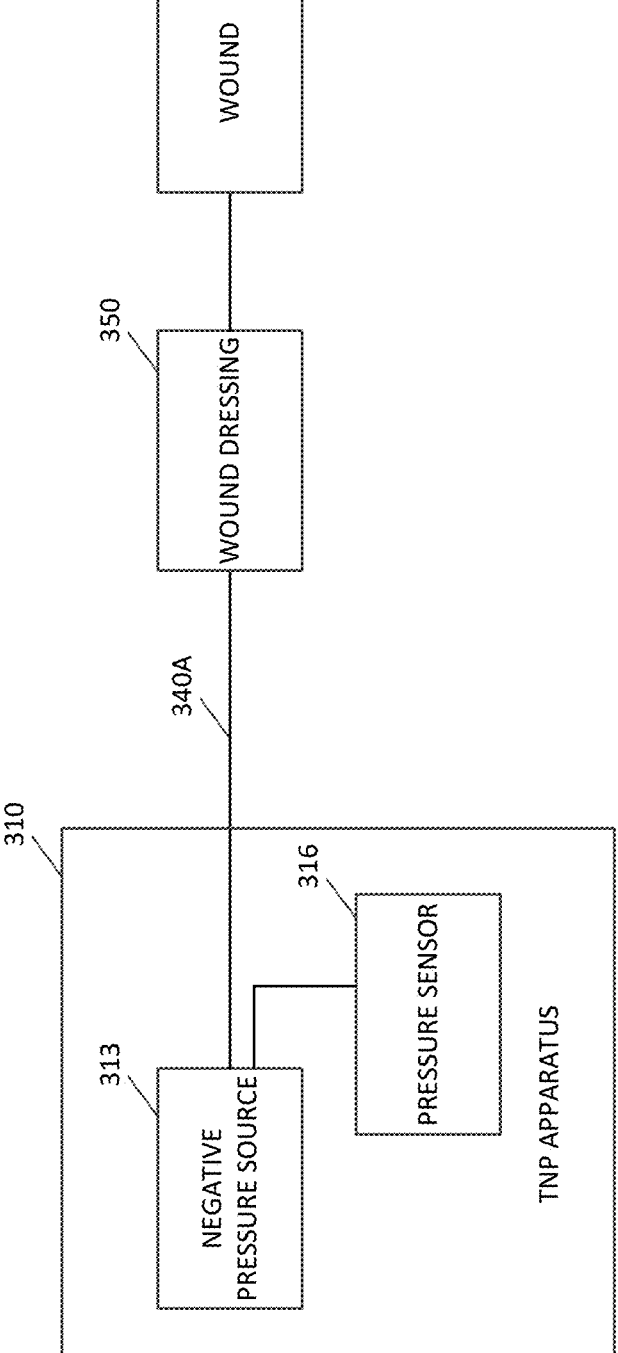

The pressure sensor 316 can be used to monitor pressure underneath a wound dressing, such as (i) pressure in a fluid flow path connecting the negative pressure source 313 and the wound dressing as illustrated by FIG. 3B, (ii) pressure at the wound dressing as illustrated by FIG. 3C, or (iii) pressure at or in the negative pressure source 313 as illustrated by FIG. 3D. As the negative pressure source 313 provides negative pressure, the negative pressure source 313 may generate pressure pulses that are propagated through the fluid flow path and detected by the pressure sensor 316. These pressure pulses may show as a change or bounce in the magnitude or frequency of a signal from the pressure sensor 316.

The controller 311 can analyze a signal output by the pressure sensor 316 to determine pressure in the fluid flow path. The controller 311 may examine the signal using one or more approaches including time domain or frequency domain calculations, such as with a digital signal processor.

The controller 311 or other circuitry of the TNP apparatus 310 may process one or more signals output by the pressure sensor 316 by filtering out noise and then dynamically amplifying the filtered one or more signals. Dynamic amplification can be performed without filtering. This may enable the features described herein to be applied to smaller wounds or weaker pressure signals. For example, the amplification can be performed by a programmable gain amplifier, which may be controlled by software or hardware.

The detection of pressure by the pressure sensor 316 can, in some instances, be enhanced by changing one or more settings of the negative pressure source 313, such as increasing or decreasing vacuum level delivered by the negative pressure source 313, stopping the negative pressure source 313, changing an operating speed of the negative pressure source 313, changing a cadence of the negative pressure source 313, combinations of the same, or the like. The controller 311 can, for example, automatically manage adjustment of the one or more settings.

Figure 3E:
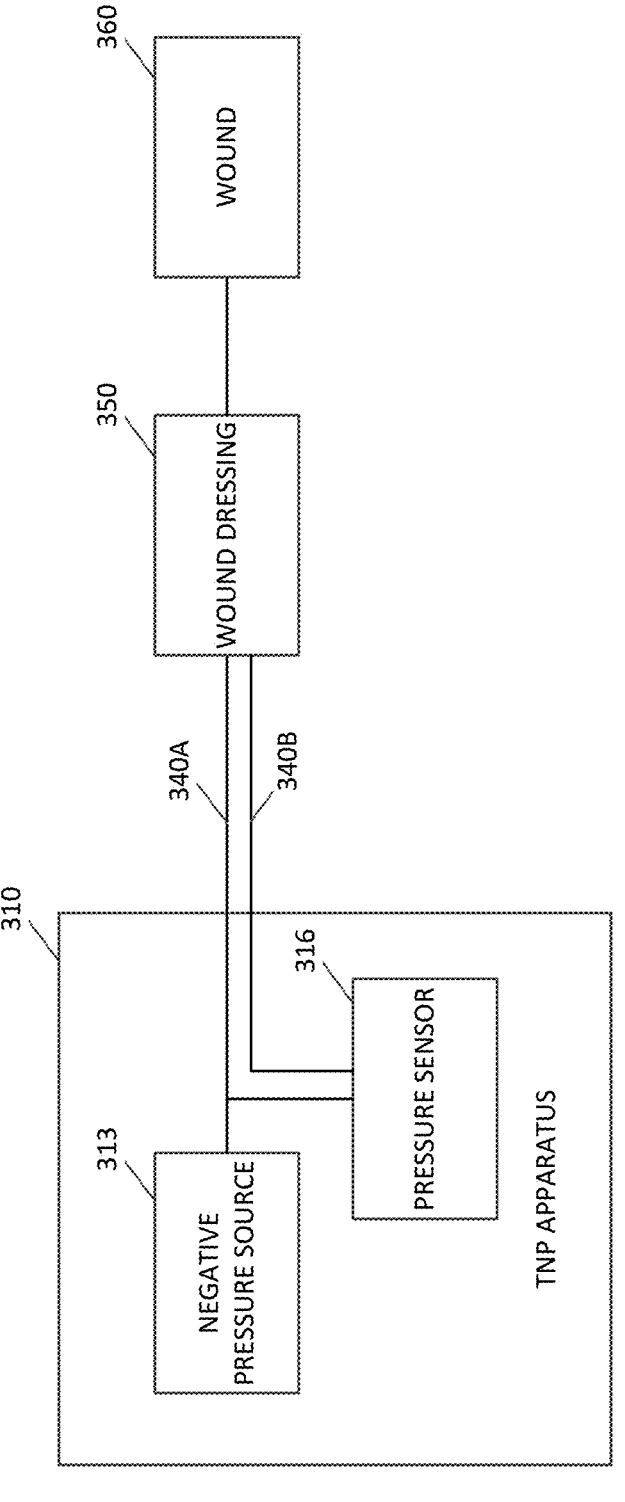

In some implementations, the pressure sensor 316 can be used in combination with another pressure sensor so that the at least two pressure sensors that are positioned in or fluidically connected to the fluid flow path to permit differential measurement of the pressure, such as illustrated by FIG. 3E. For example, a first pressure sensor can be positioned upstream of the wound (such as at or near the inlet of the negative pressure source 313C) and a second pressure sensor can be positioned to detect pressure at or near the wound or at or near a canister. This configuration can be accomplished by incorporating, in addition to one or more lumens forming a first fluid flow path connecting the negative pressure source 313 to the wound, a second fluid flow path that includes one or more lumens connecting the TNP apparatus 310 to the wound and through which the second pressure sensor can monitor pressure at or near the wound or at or near a canister. The first and second fluid flow paths can be fluidically isolated from each other. When the at least two pressure sensors are used, the rate of change of pressure (for example, in peak-to-peak pressure or maximum pressure) in the first and second fluid flow paths can be determined and the difference in pressure detected between the first and second pressure sensors can be determined. These values can be used separately or together to detect various operational conditions, such as leaks, blockages, canister full, presence of blood in the first fluid flow path or the second fluid flow path, etc. In some implementations, multiple redundant pressure sensors can be provided to protect against failure of one or more of the pressure sensors.

The transceiver 317 can be used to communicate with the data processing system 320 via a network 330. The transceiver 317 can, for example, transmit device usage data like alarms, measured pressure, or changes to a therapy program administered by the TNP apparatus 310 to the data processing system 320. The network 330 can be a communication network, such as a wireless communications network like a cellular communications network. The memory device 312 can be used to store the device usage data that may be transmitted by the transceiver 317.

The data processing system 320 can, in some implementations, analyze pressure data received from the transceiver 317 to determine whether the received pressure data is indicative of the negative pressure source 313 being in use on a patient, such as using analysis approaches as described with respect to the TNP apparatus 310. The data processing system 320 can, for instance, generate and display a report or other information reflecting data from therapy use, data from non-compliant use, or a comparison of data from therapy use versus non-compliant use. In one example, a user of the data processing system 320 may input a patient reference number or TNP apparatus number associated with a TNP apparatus, and the data processing system 320 can then provide or display data like data from therapy use or data from non-compliant use for the patient reference number or TNP apparatus number.

FIG. 3B illustrates a negative pressure therapy system 300B that includes the TNP apparatus 310 of FIG. 3A, as well as a first fluid flow path 340A, a wound dressing 350, and a wound 360. The TNP apparatus 310 can be used to treat the wound 360 using the wound dressing 350 that is in fluidic communication with the negative pressure source 313 via the first fluid flow path 340A. In particular, FIG. 3B depicts that the pressure sensor 316 can be positioned in the first fluid flow path 340A, such as at or near an inlet of the TNP apparatus 310, to measure pressure in the first fluid flow path 340A.

FIG. 3C illustrates a negative pressure therapy system 300C that differs from the negative pressure therapy system 300B in that the pressure sensor 316 can instead be positioned to measure pressure at or near the wound dressing 350, such as pressure underneath the wound dressing 350 when the wound dressing 350 is coupled to the wound 360.

FIG. 3D illustrates a negative pressure therapy system 300D that differs from the negative pressure therapy system 300B in that the pressure sensor 316 can instead be positioned to measure pressure at the negative pressure source 313. In one example, the pressure sensor 316 can be a part of and within the negative pressure source 313 to measure pressure generated by the negative pressure source 313. In another example, the pressure sensor 316 can be separate from the negative pressure source 313 and positioned to measure pressure at or near an inlet of the negative pressure source 313.

FIG. 3E illustrates a negative pressure therapy system 300E that differs from the negative pressure therapy system 300B in that the negative pressure therapy system 300E further includes a second fluid flow path 340B, and the pressure sensor 316 can be a differential pressure sensor or include two pressure sensors. If the pressure sensor 316 may include the two pressure sensors, one of the two pressure sensors of the pressure sensor 316 can be positioned in the first fluid flow path 340A to measure pressure in the first fluid flow path 340A, and the other of the two pressure sensors the pressure sensor 316 can be positioned in the second fluid flow path 340B to measure pressure in the second fluid flow path 340B. If the pressure sensor 316 may be the differential pressure sensor, the pressure sensor 316 can be fluidicially connected to the first fluid flow path 340A and the second fluid flow path 340B. The first fluid flow path 340A can thus be used by the negative pressure source 313 to provide negative pressure to the wound dressing 350, and the second fluid flow path 340B can be used primarily by the pressure sensor 316 to measure pressure at or near the wound dressing 350, such as under the wound dressing 360. The pressure sensor 316 can thereby be used by the TNP apparatus 310 to perform differential measurement of pressure between pressure supplied by the negative pressure source 313 and pressure at or near the wound dressing 350.

Figure 3F:
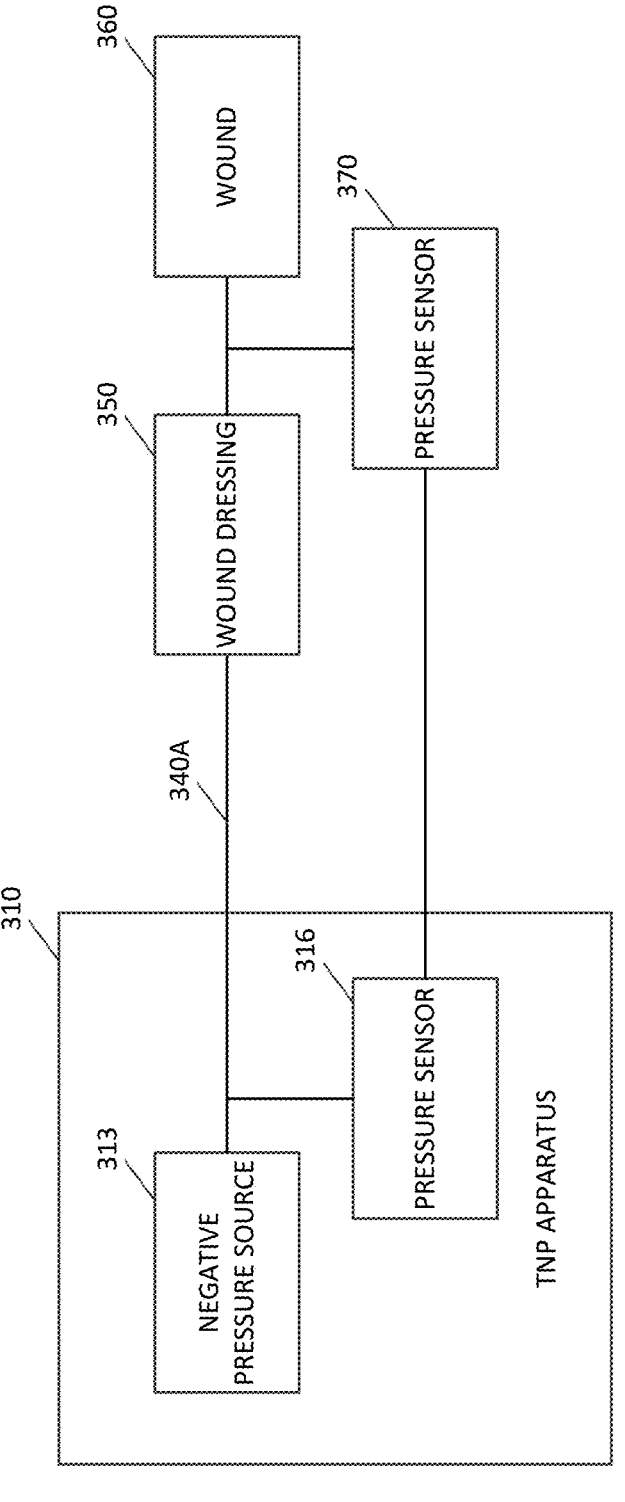

FIG. 3F illustrates a negative pressure therapy system 300F that differs from the negative pressure therapy system 300B in that the negative pressure therapy system 300F can further include an additional pressure sensor 370 positioned to measure pressure at or near the wound dressing 350, such as pressure underneath the wound dressing 350 when the wound dressing 350 is coupled to the wound 360. The additional pressure sensor 370 can generate and output a signal to the TNP apparatus 310 responsive to the pressure measured at the wound dressing 350. The pressure sensor 316 and the additional pressure sensor 370 can thus be used by the TNP apparatus 310 to perform differential measurement of pressure between pressure supplied by the negative pressure source 313 and pressure at or near the wound dressing 350.

Figure 3G:
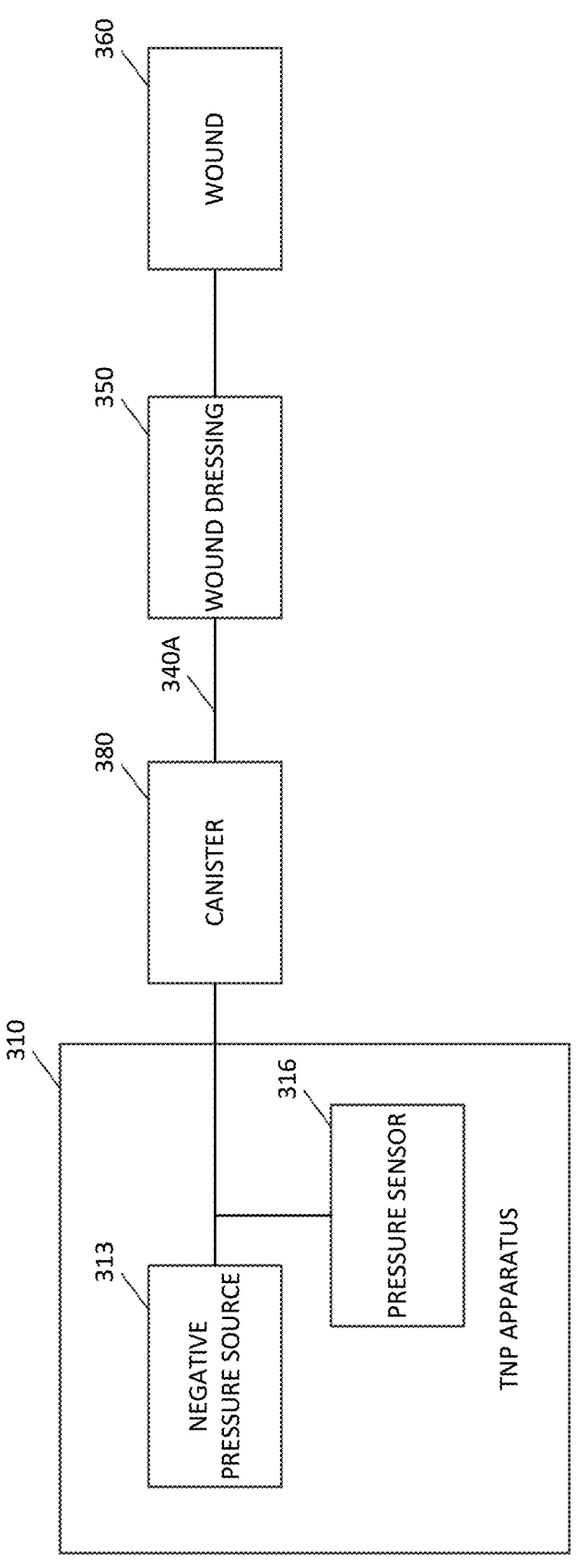

FIG. 3G illustrates a negative pressure therapy system 300G that differs from the negative pressure therapy system 300B in that a canister 380 can be coupled between the negative pressure source 313 and the wound dressing 350 in the first fluid flow path 340A. The canister 380 can collect exudate removed from the wound 360. The examples of FIGS. 3C-3F can be similarly modified to also include the canister 380, in some implementations.

Figure 4:
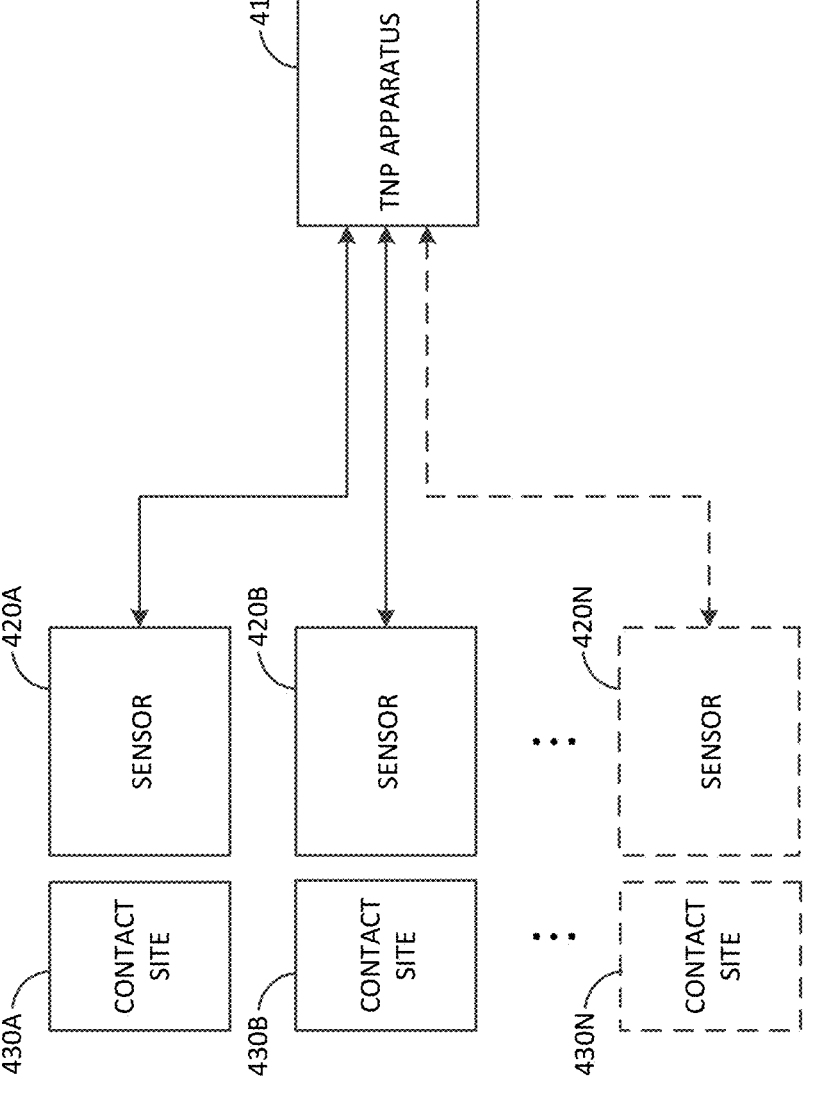
FIG. 4 illustrates components of a negative pressure therapy system that includes multiple sensors according to some embodiments.

FIG. 4 illustrates a negative pressure therapy system 400 that includes a TNP apparatus 410 and sensors 420A, 420B, . . . , 420N. The sensors 420A, 420B, . . . , 420N can advantageously be used, in certain embodiments, to confirm coupling to or use of the TNP apparatus 410 on a patient. The TNP apparatus 410 can be similar to or the same as the TNP apparatus 310 in some embodiments. One of the sensors 420A, 420B, . . . , 420N can be similar to or the same as the pressure sensor 316 in some embodiments. One of the sensors 420A, 420B, . . . , 420N can be similar to or the same as the pressure sensor 370 in some embodiments.

The sensors 420A, 420B, . . . , 420N can be respectively detecting from contact sites 430A, 430B, . . . , 430N of the patient or responsive to the patient. The sensor 420A can, for instance, be detecting from the contact site 430A, and the sensor 420B can be detecting from the contact site 430B while the sensor 420N can be detecting from the contact site 430N. The contact sites 430A, 430B, . . . , 430N can include tissue sites of the patient (for instance, an internal or external tissue of the patient at a wound, a limb, or a head of the patient), items attached to the patient (for instance, clothing or jewelry), or part of the TNP apparatus 410 or a related component like a canister. One or more of the sensors 420A, 420B, . . . , 420N may be incorporated as part of the wound dressing or configured to couple to the wound dressing.

The sensors 420A, 420B, . . . , 420N can include, for example, one or more of a pressure sensor, an acoustic sensor, a chemical sensor, an electric current sensor, electric potential sensor, an impedance sensor, a magnetic sensor, an optical sensor, a color sensor, a pressure sensor, a piezo-electric sensor, a thermometer, a thermal sensor, a proximity sensor, a biosensor, a strain gauge, combinations of the same, or the like. The sensors 420A, 420B, . . . , 420N can be the same sensors placed to detect at different locations or different sensors in some implementations.

Each of the sensors 420A, 420B, . . . , 420N can transmit, via wireless or wired communication, one or more signals responsive to a corresponding monitored one of the contact sites 430A, 430B, . . . , 430N to the TNP apparatus 410. The one or more signals can, for instance, be responsive to a physiological condition of the patient or movement by the patient. In turn, the TNP apparatus 410 can process the one or more signals to determine whether the one or more signals from two or more of the sensors 420A, 420B, . . . , 420N indicate that the TNP apparatus 410 or related component like a wound dressing is coupled to the patient or in compliant use on the patient. The TNP apparatus 410 can, for example, determine whether each or at least a subset of two or more of the sensors 420A, 420B, . . . , 420N provide physiologically acceptable signals (for example, signals responsive to patient activity like patient respiration, pulse, or motion) to the TNP apparatus 410 that indicate successful coupling to or association of the TNP apparatus 410 with the patient.

Wound Coupling Detection

Figure 5:
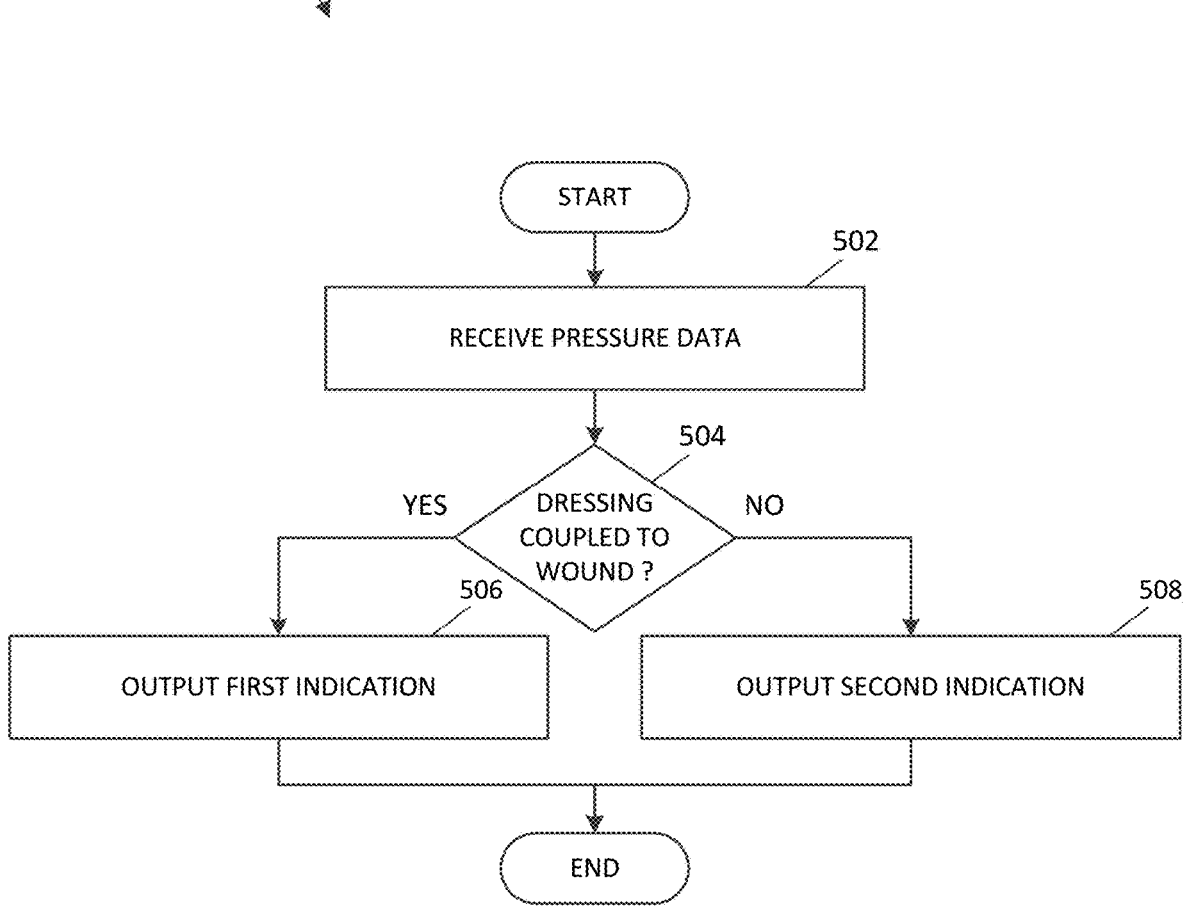
FIG. 5 illustrates a wound coupling detection process according to some embodiments.

FIG. 5 illustrates a wound coupling detection process 500 performable by a device, such as the pump assembly 150 of FIG. 1, the pump assembly 230 of FIG. 2A-C, the TNP apparatus 310 of FIG. 3A, or other pump assemblies like those described in U.S. Patent Publication Nos. 2016/0136339 and 2016/0184496 that were previously incorporated herein by reference in their entireties. For convenience, the wound coupling detection process 500 is described in the context of the TNP apparatus 310 of FIG. 3A, but may instead be implemented in other systems described herein or by other systems not shown.

The wound coupling detection process 500 can enable the TNP apparatus 310 to automatically determine whether a wound dressing coupled to the TNP apparatus 310 is coupled to a wound of a patient. The TNP apparatus 310 can advantageously, in certain embodiments, output a first indication when the wound dressing is determined to be coupled to a wound or a second indication different from the first indication when the wound dressing is determined not to be coupled to a wound.

At block 502, the process 500 can receive pressure data. For example, the controller 311 can receive pressure data indicative of a magnitude of pressure measured in a fluid flow path coupling the negative pressure source 313 to a wound dressing. The pressure can be measured, for instance, by the pressure sensor 316 using measurement approaches as described herein or in U.S. Patent Publication Nos. 2016/0136339 and 2016/0184496, which were previously incorporated herein by reference in their entireties. The pressure sensor 316 can communicate information via a wire or wirelessly to the controller 311. In certain implementations, the pressure sensor 316 can be positioned at or near the wound and wirelessly communicate information to the controller 311. In some embodiments, pressure sensor data includes one or more magnitudes of pressure measured over a duration of time, such as 0.5 seconds, 1 second, 3 seconds, and the like.

At block 504, the process 500 can determine whether a dressing is coupled to a wound. For instance, the controller 311 can determine from the pressure data, such as from a change in the magnitude over time, whether the wound dressing is coupled to a wound of a patient.

In one example, the controller 311 can compare a measure of the irregularity of the change in the magnitude over time to one or more thresholds to determine whether wound dressing is coupled to the wound (and in some instances, perform the comparison multiple times to prevent false positives due to errant pressure readings, noise, and the like). The measure of the irregularity can be responsive to the change in the magnitude over a duration of at least 1 second, 10 seconds, 30 seconds, 1 minute, or 5 minutes. The controller 311 can perform a statistical operation, a trending operation, a filtering operation, a cumulative summation operation, or a low-pass filtering operation on the magnitude over time to generate the measure of irregularity. The controller 311 can determine that the wound dressing is coupled to the wound in response to determining that the measure of irregularity satisfies a threshold corresponding to the chaotic condition or does not satisfy a threshold corresponding to the steady state condition. On the other hand, the controller 311 can determine that the wound dressing is not coupled to the wound in response to determining that the measure of irregularity does not satisfy the threshold corresponding to the chaotic condition or satisfies the threshold corresponding to the steady state condition. The one or more thresholds to which the measure of the irregularity is compared, moreover, can vary over time (for example, automatically adjust as the patient heals) or be set responsive to operating conditions for the TNP apparatus 310 (for example, adjust to become more or less sensitive to background noise) or health needs of the patient (for example, adjust depending on a size of a wound, gender of the patient, or age of the patient).

In yet another example, the controller 311 can compare the magnitude over time to one or more pressure patterns, such as one stored in the memory device 312, to determine whether the wound dressing is coupled to the wound. One pressure pattern, for instance, can be indicative of pressure in the fluid flow path when the wound dressing is coupled to the wound, and another different pressure pattern can be indicative of pressure in the fluid flow path when the wound dressing is not coupled to the wound. The degree of similarity of the magnitude over time relative to the one or more pressure patterns can be used to assign the magnitude over time as reflecting either the wound dressing is or is not coupled to the wound.

At block 506, the process 500 can output a first indication. For example, in response to determining that the wound dressing is coupled to the wound, the controller 311 can output a first indication indicative of the wound dressing being coupled to the wound. The first indication can denote compliant usage of the TNP apparatus 310 in some instances. The first indication can be output, for example, by one or more of: outputting the first indication for storage in the memory device 312, transmitting the first indication to the data processing system 320 via the transceiver 317, outputting the first indication for presentation to a user via the user interface 314, or storing the first indication in association with device usage data of the TNP apparatus 310. The outputting of the first indication can additionally control operations of the TNP apparatus 310, such as to enable continued activation of the negative pressure source 313.

At block 508, the process 500 can output a second indication. For example, in response to determining that the wound dressing is not coupled to the wound, the controller 311 can output a second indication indicative of the wound dressing not being coupled to the wound. The second indication can denote non-compliant usage of the TNP apparatus 310 in some instances. The second indication can be output, for example, by one or more of: outputting the second indication for storage in the memory device 312, transmitting the second indication to the data processing system 320 via the transceiver 317, outputting the second indication for presentation to a user via the user interface 314, or storing the second indication in association with device usage data of the TNP apparatus 310. The outputting of the second indication can additionally control operations of the TNP apparatus 310, such as to cause deactivation of the negative pressure source 313 because the TNP apparatus 310 may be being used in a non-compliant manner.

The process 500 can examine data from another sensor as described, for instance, with respect to FIG. 4 to provide additional information or confidence as to whether the TNP apparatus 310 may be being used in a compliant or non-compliant manner. For example, if another sensor associated with the TNP apparatus 310 detects a signal reflecting a pulse or respiration of a patient, the TNP apparatus 310 may have further confidence and information that the TNP apparatus 310 is being used in a compliant manner rather than a non-compliant manner.

Figure 6:
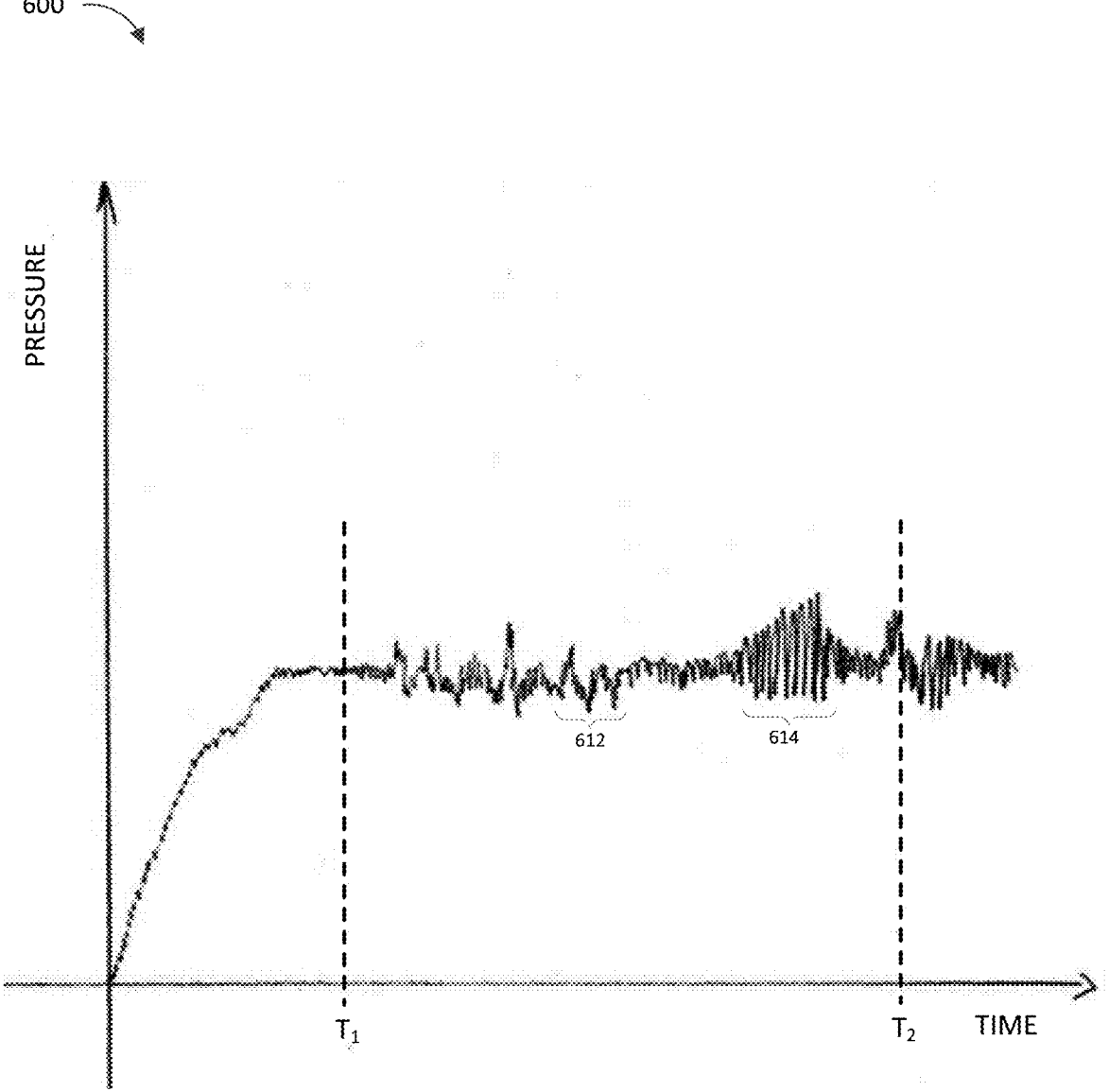
FIGS. 6 and 7 illustrate example pressure versus time curves for a negative pressure therapy system according to some embodiments.

FIG. 6 illustrates an example pressure versus time curve 600 for a TNP system in which a negative pressure source of a TNP apparatus, such the TNP apparatus 310, is in use on a wound of a patient. As can be seen from FIG. 6, once the negative pressure source has been activated for a period of time, at time $T_1$ the magnitude of pressure in the fluid flow path can generally fluctuate around a target pressure level. The magnitude of pressure in the fluid flow path, however, can be substantially chaotic and unpredictable from time $T_1$ to $T_2$ for a number of reasons. The patient can be continuously moving due to physical adjustments of the position, breathing, or pulse, thus affecting, for instance, the geometry of the wound, the dressing seal, etc. As a result, the volume of the wound may continuously be undergoing minor changes which can result in changes in the magnitude of pressure. Further, the wound can produce exudate, which upon entering the fluid flow path can cause a gas volume to decrease. Because the gas volume can represent the compressible volume in the system, this compressible volume can act as a damper to pressure spikes created by the negative pressure source and movement of the patient so that the pressures spikes become increasingly large due to reduced damping. In addition, liquid can leave the wound dressing and travel up through the fluid flow path in slugs, and these slugs can affect (for example, increase in magnitude or frequency) the pressure spikes. Overall, this can result is a relatively significant amount of noise in the pressure readings. The magnitude of pressure depicted by FIG. 6 may thus be reflective of a chaotic condition from time $T_1$ to $T_2$ rather than a steady state condition. In addition or alternatively, other characteristics of pressure, such as frequency, can be monitored for changes. For example, from time $T_1$ to $T_2$, frequency of the pressure signal is smaller in over the time duration 612 than the time duration 614.

In one implementation, the TNP apparatus 310 can monitor the noise described in the preceding paragraph to determine whether the negative pressure source is connected to a patient. Thus, the TNP apparatus 11 can, for example, flag usage data and logging of events as either (i) patient data or (ii) device misuse. The TNP apparatus 310 can, in some instances, use statistical techniques trending techniques or filtering techniques, such as cumulative sum (Cusum) or low-pass filtering, to determine if the pressure readings may be in steady state (not attached to a wound) or chaotic (attached to a wound).

Figure 7:
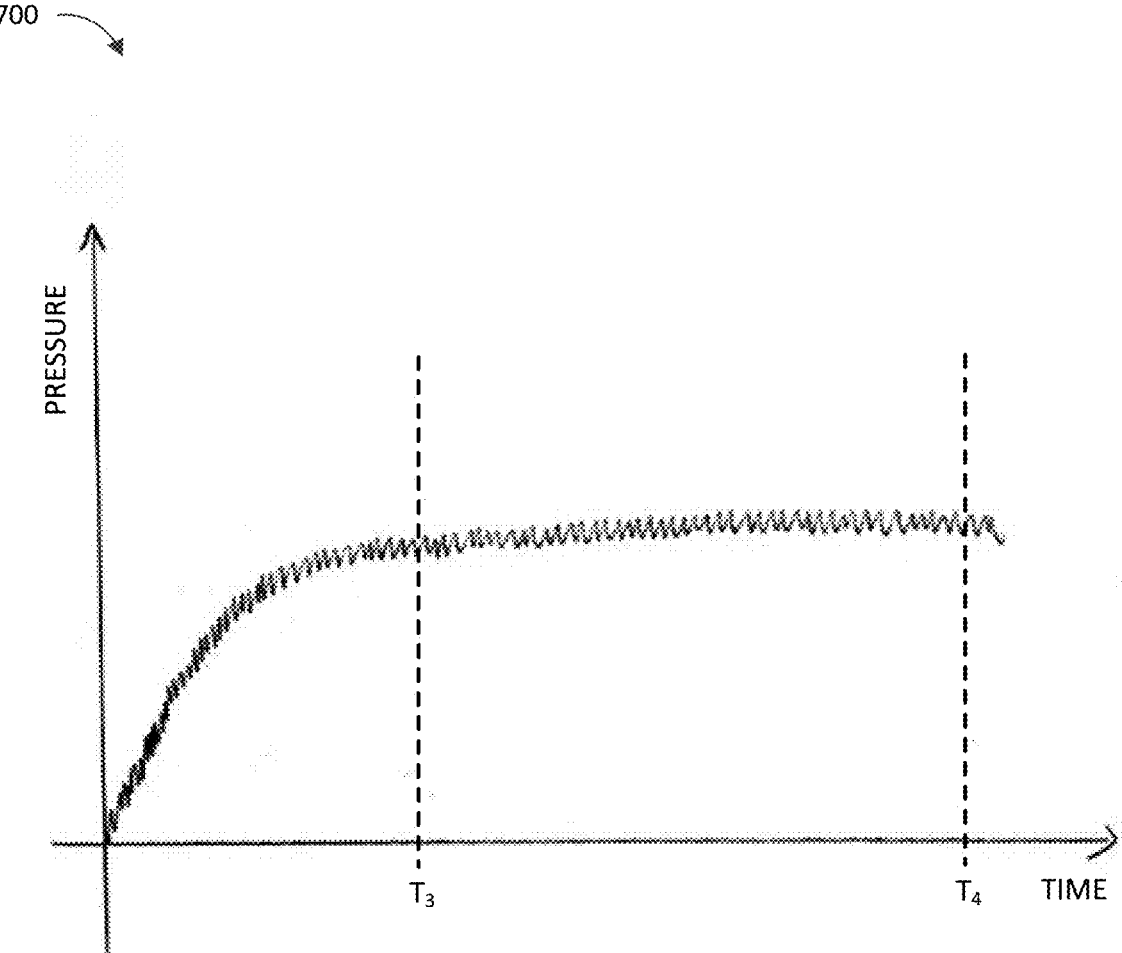

FIG. 7 illustrates an example pressure versus time curve 700 for a TNP system in which a negative pressure source of a TNP apparatus, such the TNP apparatus 310, is not in use on a wound of a patient. As can be seen from FIG. 7, once the negative pressure source has been activated for a period of time, at time $T_3$ the magnitude of pressure in the fluid flow path can generally fluctuate around a target pressure level. The frequency can generally fluctuate around a particular frequency value. The magnitude of pressure in the fluid flow path, however, can be less chaotic and more predictable (such as from time $T_3$ to $T_4$) than when the TNP apparatus is in use on the wound, for at least the reasons described in the preceding two paragraphs as well as other reasons described herein. The magnitude of pressure depicted by FIG. 7 may thus be reflective of a steady state condition from time $T_3$ to $T_4$ rather than a chaotic condition.

From comparing pressure characteristic depicted from time $T_1$ to $T_2$ in FIG. 6 and from time $T_3$ to $T_4$ in FIG. 7, the following features can be noted. The characteristics of pressure from time $T_1$ to $T_2$ in FIG. 6 can have one or more of a greater pressure magnitude variation, more pressure frequency variation over time, higher pressure magnitude components (such as, spikes), or greater randomness than the magnitude or frequency of pressure as compared to pressure variations over time $T_3$ to $T_4$ in FIG. 7.

In some embodiments, time series analysis algorithms such Auto Regressive Integrated Moving Average (ARIMA), Generalized Autoregressive Conditional Heteroskedasticity (GARCH), or Cusum (or cumulative sum) can be used to detect use on a wound of a patient. Cusum can be defined as the running sum of the difference between each sample and the mean (e.g., in the absence of change, Cusum is zero). Cusum can be used to track variations in the underlying variable.

Cusum can be determined in a number of ways. In certain implementations, non-causal Cusum uses the mean calculated from the entire duration of an input signal, which requires knowledge of all samples before the difference from the mean can be calculated. Non-causal Cusum may not be suitable for real-time monitoring and detection and classification unless an estimate of the mean from prior analysis can be used. Non-causal Cusum can starts and end with a value of zero.

The sliding causal Cusum can be determined using a sliding window to estimate the mean. Initial step change can yield the first departure from zero, rather than resulting in a change of gradient as in the non-causal Cusum. Sliding causal Cusum can produce data within durations of time that are shorter than with non-causal Cusum. Sliding causal Cusum may allow tighter bounds to be used to detect changes and may be less prone to rounding and rollover errors (e.g., numerical errors that may result from use of longer sequences of data).

The cumulative causal Cusum determination may use all preceding samples from the start of a time duration to the current sample to estimate the mean for the current sample in some embodiments. This version of Cusum can be a compromise between the foregoing two versions, and may be smoother than sliding causal Cusum but not ending at a zero value.

A TNP apparatus can, for example, be connected to a wound model and one or more sensors can be used to detect one or more of the parameters in Table 1. These parameters can include pressure measurements, level of activity measurements, and the like obtained during operation of the negative pressure wound therapy system. In some embodiments, the level of activity can include one or more parameters of an actuator (e.g., motor) of the negative pressure source (e.g., pump), such as current (or voltage) of a motor drive signal, PWM signal, and motor speed. The apparatus can be operated under the conditions of changing one of vacuum level provided by the negative pressure source, rate of water removed from the wound, rate of exudate removed from the wound, rate of blood removed from the wound, or gas (e.g., air) leak rate in the fluid flow path while maintaining the other parameters constant. This way, operational parameters can be determined, statistics can be computed and analyzed (e.g., by using Cusum analysis), and the most appropriate statistic(s) for detecting use on a wound of a patient can be selected. In addition, in some embodiments, statistical properties of one or more of the statistics in Table 1 are calculated. These statistical properties can include one or more of mean, standard deviation, skewness (third statistical moment), kurtosis (fourth statistical moment), minimum, and maximum.

TABLE 1

| Input signals and statistics | |
| --- | --- |
| Input Signal | Statistic |
| Vacuum Pressure | Raw |
| Vacuum Pressure | Mean |
| Vacuum Pressure | Standard Deviation |
| Vacuum Pressure | Peak to Peak |
| Current | Raw |
| Current | Mean |
| Current | Standard Deviation |
| Current | Peak to Peak |
| PWM | Raw |
| PWM | Mean |
| PWM | Standard Deviation |
| PWM | Peak to Peak |
| Impulse (Motor Speed) | Raw |
| Impulse (Motor Speed) | Mean |
| Impulse (Motor Speed) | Standard Deviation |
| Impulse (Motor Speed) | Peak to Peak |
| Tick Rate (Motor Speed) | Raw |

Using correlation and fitness analysis is described, for instance, in International Patent Application No. PCT/US2017/017538 titled "SYSTEMS AND METHODS FOR DETECTING OPERATIONAL CONDITIONS OF REDUCED PRESSURE THERAPY," filed on Feb. 10, 2017, and published as US 2020/0376175, the entirety of which is incorporated by reference, the following statistics can be selected for detection and classification of one or more operational conditions of a TNP apparatus:

TABLE 2

| Statistics used for detection and classification | |
| --- | --- |
| Operational Condition | Statistic |
| Vacuum level | Mean of the raw vacuum (e.g., 802) |
| Gas leak rate | Standard deviation of the rolling mean of motor current (e.g., 804) |
| Water/Exudate rate | Kurtosis of the rolling standard deviation of pump speed (e.g., 806) |
| Blood rate | Standard deviation of the rolling standard deviation of the motor current (e.g., 808) |

Figure 8:
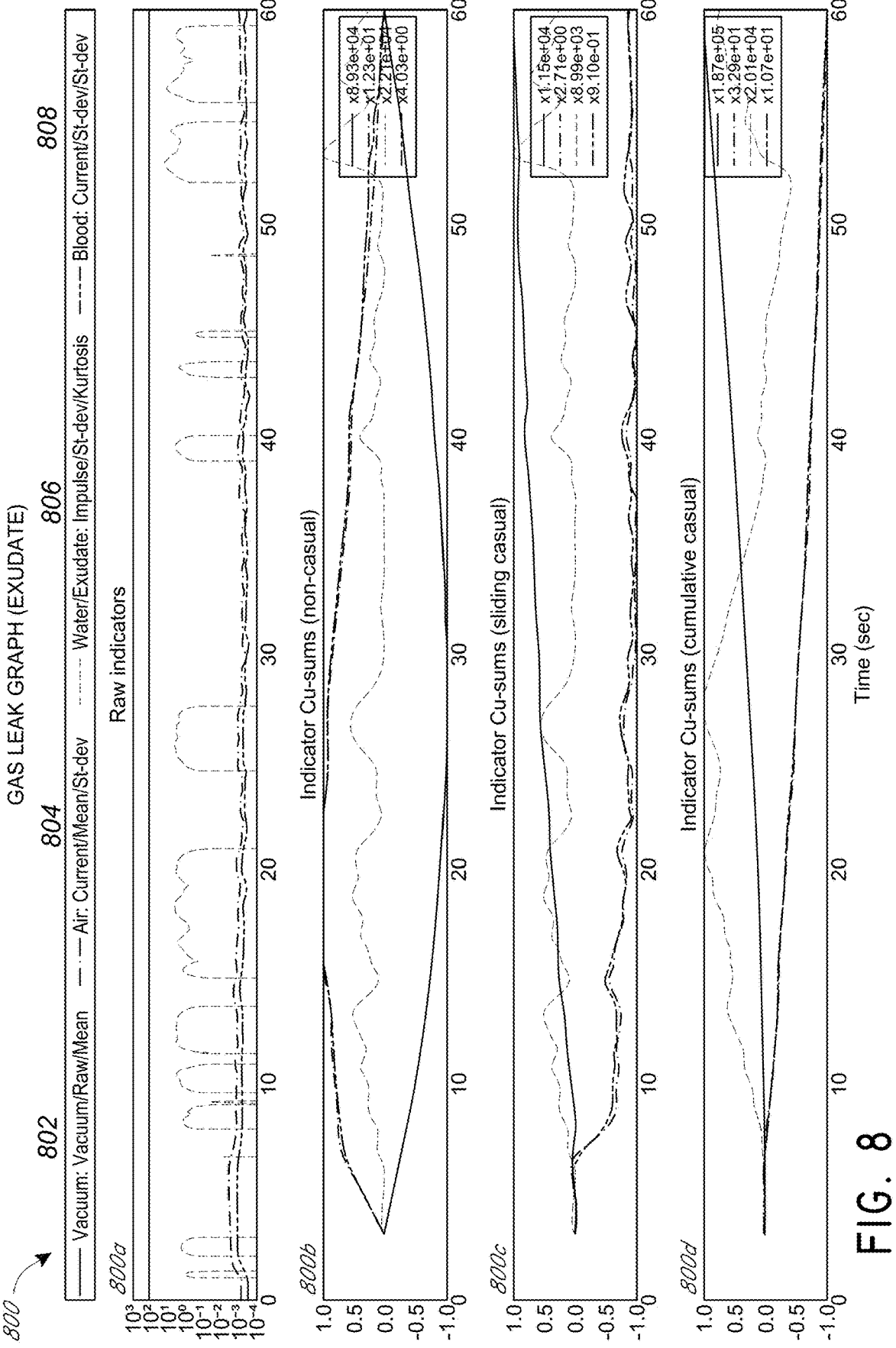
FIGS. 8, 9, and 10 illustrate variations due to a gas leak, change in fluid rate, and change in vacuum level according to some embodiments.
Figure 9:
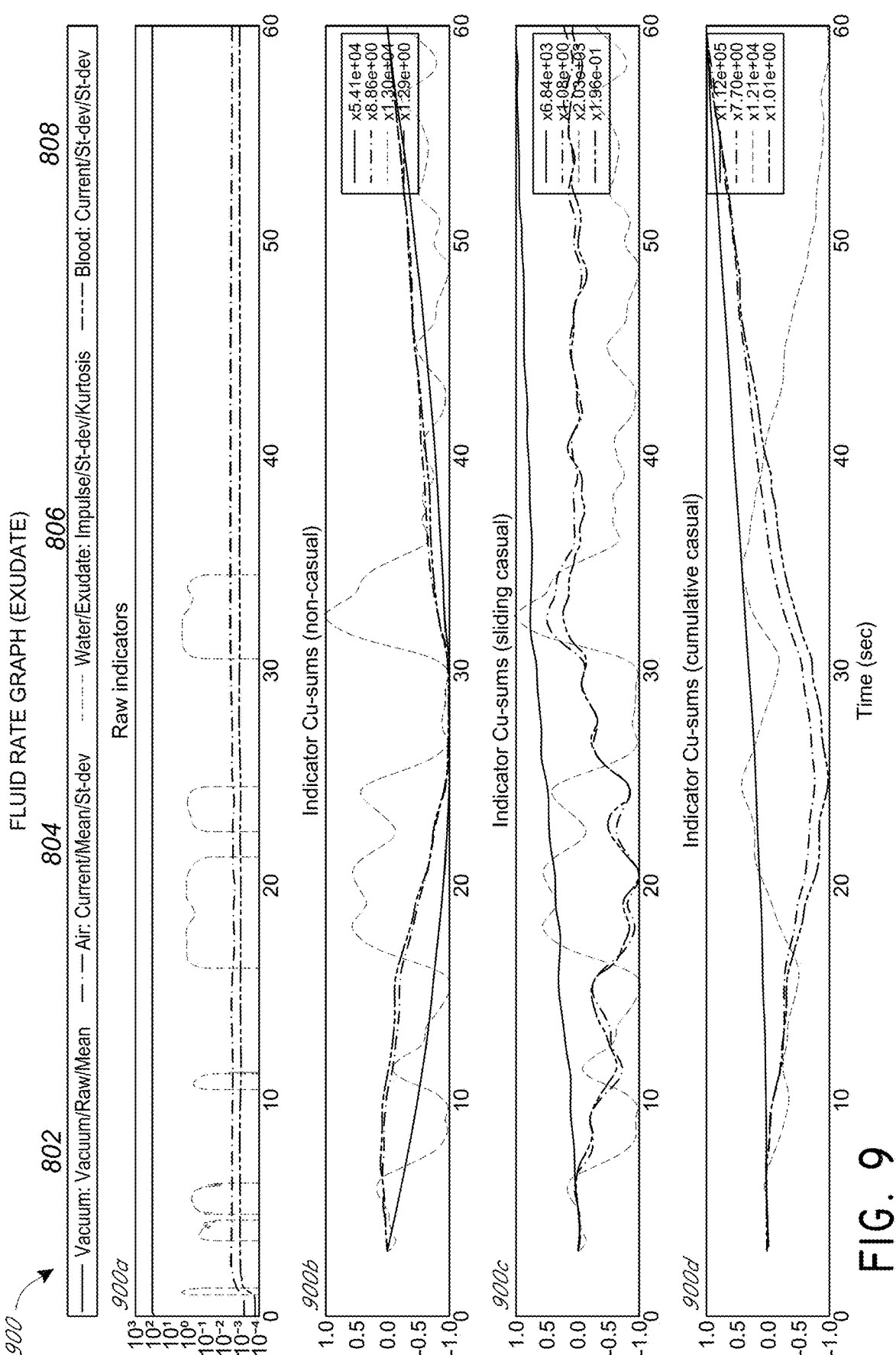
Figure 10:
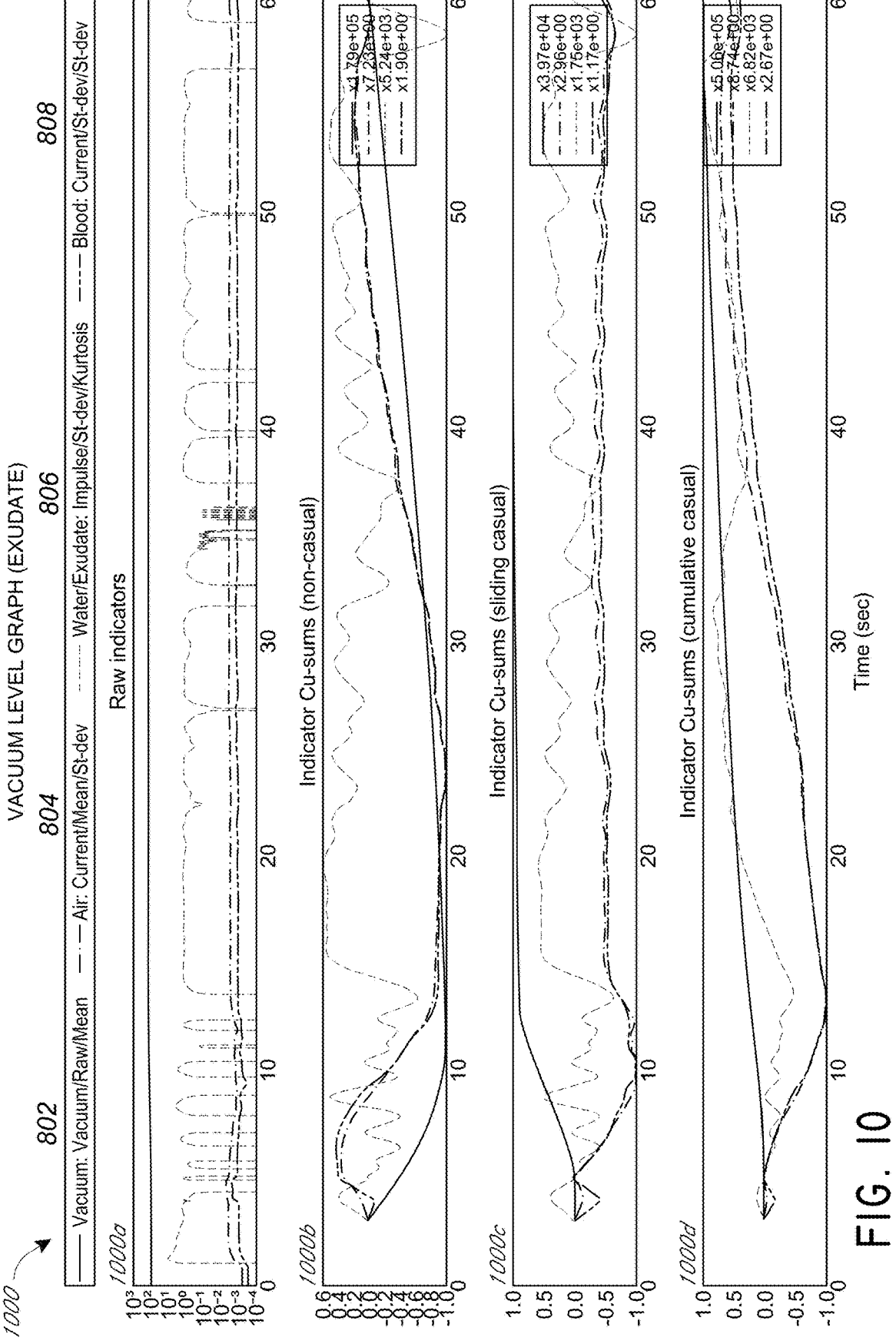

For example, in the graphs illustrated in FIGS. 8-10, a TNP apparatus was operated initially in steady-state and thereafter one of the operational parameters or variables was changed. In FIG. 8, the intensity of gas (e.g., air) leak in the fluid flow path has been changed (e.g., from 60 sccm to 180 sccm at around 5 seconds) and collected and analyzed data is used to perform detection of an abrupt increase in the leak rate. In FIG. 9, flow rate of fluid (e.g., exudate) has been changed (e.g., bolus of fluid introduced into the fluid flow path at around 5 seconds) and collected and analyzed data is used to perform detection of change in the fluid flow rate. In FIG. 10, vacuum level produced by the negative pressure source has been changed (e.g., from –80 mmHg to –120 mmHg at around 18 seconds) and collected and analyzed data is used to perform detection of change in vacuum pressure in the fluid flow path.

FIG. 8 illustrates detection 800 of a gas leak when exudate is being aspirated from a wound according to some embodiments. Four plots 800a, 800b, 800c, and 800d are illustrated corresponding to, respectively, raw (or unprocessed) values of the statistics in Table 2 and non-causal Cusum, sliding causal Cusum, and cumulative causal Cusum of the statistics in Table 2. In plots 800a-d, curves 802 represent raw and Cusum values of mean of raw vacuum, curves 804 represent raw and Cusum values of standard deviation of the rolling mean of motor current, curves 806 represent raw and Cusum values of kurtosis of rolling standard deviation of pump speed, and curves 808 represent standard deviation of rolling standard deviation of motor current. X-axes in the plots 800a-d corresponds to time duration (e.g., 60 seconds). Y-axis in plot 800a represents logarithmic scale (to normalized different raw values of the statistics), and y-axes in plots 800b-d are linearly scaled (or normalized) so that Cusum values are in the range (–1.0, 1.0). Plots 800a-d capture data corresponding to a change (e.g., increase) in the gas leak rate (e.g., from 60 sccm to 180 sccm at around 5 seconds).

FIG. 9 illustrates detection 900 of a change in fluid rate when exudate is being aspirated from a wound according to some embodiments. Four plots 900a-d are illustrated corresponding to, respectively, raw (or unprocessed) values of the statistics in Table 2 (labeled 802, 804, 806, and 808) and non-causal Cusum, sliding causal Cusum, and cumulative causal Cusum of the statistics. Plots 800a-d capture data corresponding to a change (e.g., increase) in exudate flow rate due to bolus of exudate being released into the fluid flow path (e.g., at around 5 seconds).

FIG. 10 illustrates detection 1000 of a change in vacuum level when exudate is being aspirated from a wound according to some embodiments. Four plots 1000a-d are illustrated corresponding to, respectively, raw (or unprocessed) values of the statistics in Table 2 (labeled 802, 804, 806, and 808) and non-causal Cusum, sliding causal Cusum, and cumulative causal Cusum of the statistics. Plots 1000a-d capture data corresponding to a change (e.g., increase) in vacuum level provided by the pump (e.g., from −80 mmHg to −120 mmHg at around 18 seconds).

In certain implementations, as described in International Patent Application No. PCT/US2017/017538, similar plots can be obtained when another type of fluid, such as water or blood, is introduced into the fluid flow path.

Detection of one or more operational conditions described herein can moreover be used for detection of use on a wound of a patient. For example, with reference to FIG. 8, various Cusums (non-causal, sliding causal, and cumulative causal) for the standard deviation of the rolling mean of motor current (804) are responsive to the increase in the gas leak around 5 seconds. Non-causal Cusum illustrated in 800*b* sharply increases between about 5 and 8 seconds, flattens out between about 9 and 30 seconds, and then gradually decreases after about 30 seconds. Sliding causal Cusum illustrated in 800*c* stays relatively flat between about 5 and 7 seconds, sharply decreases at 9 seconds, and then stays relatively flat. Cumulative causal Cusum illustrated in 800*c* stays relatively flat between about 5 and 8 seconds and linearly or monotonically decreases thereafter. Any of such patterns, including sharp, gradual, or linear changes (increases or decreases), can be compared to one or more thresholds to detect changes in the gas leak rate. Detection of such changes in the gas leak rate can be indicative of use on a wound of a patient.

As another example, with reference to FIG. 9, various Cusums (non-causal, sliding causal, and cumulative causal) for the kurtosis of the rolling standard deviation of pump speed (806) are responsive to the increase in the exudate flow rate at around 5 seconds. As illustrated in plots 900*b-d*, curve 806 is substantially periodic after about 6 seconds and reaches several distinctive peaks around 20, 25, and 35 seconds. Such patterns indicating change in the exudate flow rate can be detected, by, for example, comparison to one or more thresholds, and can be used to provide indication of use on a wound of a patient.

As yet another example, with reference to FIG. 10, various Cusums (non-causal, sliding causal, and cumulative causal) for the mean vacuum (802) are responsive to the increase in the vacuum level at around 18 seconds. Non-causal Cusum illustrated in 1000*b* linearly or monotonically increases after about 18 seconds. Cumulative causal Cusum illustrated in 1000*c* stays linearly or monotonically increases after about 18 seconds. Any of such patterns, including linear changes (increases or decreases), can be compared to one or more thresholds to detect changes in the vacuum level. Detection of such changes in the gas leak rate can be indicative of use on a wound of a patient.

Presence of blood or change in flow rate of blood can detected based on, for example, the standard deviation of the rolling standard deviation of the motor current (808) as described in International Patent Application No. PCT/US2017/017538. Detection of any one or more of changes in the gas leak rate, vacuum level, exudate flow rate, or blood flow rate can be used to provide indication of use on a wound of a patient.

Figure 11:
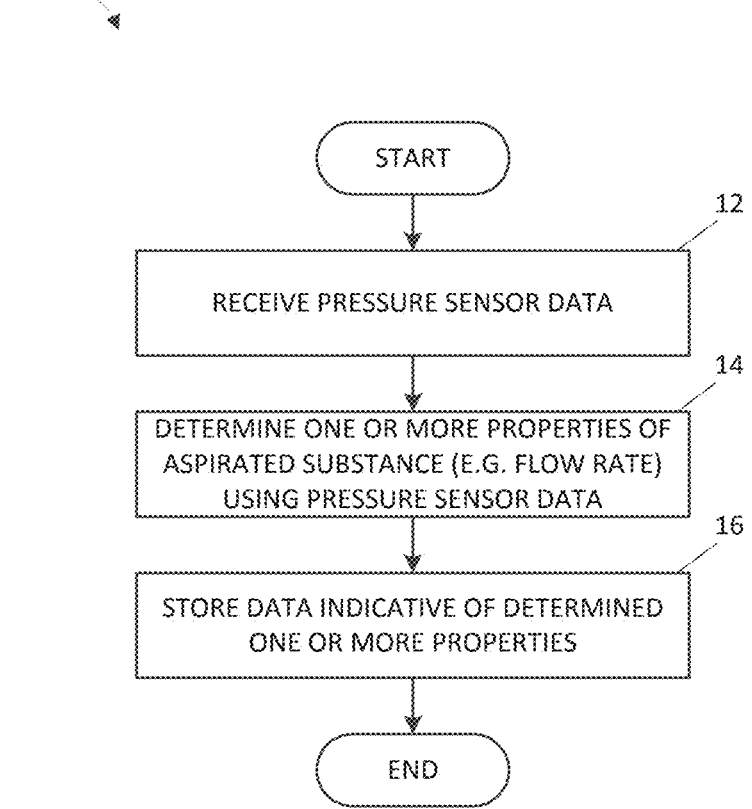
FIG. 11 illustrates a flow estimation process according to some embodiments.

FIG. 11 illustrates a flow estimation process 10 performable by a device, such as the pump assembly 150 of FIG. 1, the pump assembly 230 of FIG. 2, or other pump assemblies described herein. In some embodiments, the process 10 can be implemented by one or more of the processors described herein. For convenience, the flow estimation process 10 is described in the context of system 100 of FIG. 1, but may instead be implemented in other systems described herein or by other computing systems not shown.

The flow estimation process 10 can enable the pump assembly 150 to determine an estimated composition of a substance in the fluid flow path so that the pump assembly 150 can differentiate between various substances (e.g., blood versus liquid or gaseous exudate) in the fluid flow path. For example, the pump assembly 150 can advantageously, in certain embodiments, output an indication of presence of blood in the fluid flow path (such as in the dressing, the tube 140, or in the canister (if present)) for display to a user of the pump assembly 150 or adjust an operation of the pump assembly 150, such as an operation of a source of negative pressure of the pump assembly 150 (e.g., pause operation of the source of negative pressure), in view of detecting the presence of blood in the flow fluid path.

At block 12, the process 10 can receive the pressure sensor data indicative of a measured pressure in the fluid flow path, which includes the tube 140. The pressure can be measured, for instance, by one or more of the pressure sensors described herein. The one or more pressure sensors can communicate information via a wire or wirelessly. In certain implementations, one of the pressure sensors can be positioned at or near the wound and wirelessly communicate information to the pump assembly 150. In some embodiments, pressure sensor data includes multiple pressure values taken over a duration of time, such as 1 microsecond or less, 1 millisecond, 0.5 seconds, 1 second, 3 seconds or more, and the like.

At block 14, the process 10 can determine one or more properties of a substance in the fluid flow path using the pressure sensor data. For example, the processor can examine a rate of change of pressure (e.g., in peak-to-peak pressure or maximum pressure) in the fluid flow path using the pressure sensor data to determine changes in the flow. The measured pressure can, for instance, be relatively higher when blood or tissue clots enter or flow in the fluid flow path than when liquid or gaseous exudate enters or flows in the fluid flow path, and thus the rate of change of the pressure can indicate presence of blood or tissue clots in the fluid flow path. Because blood or tissues clots have higher density than liquid or gaseous exudate, the rate of flow decreases and the fluid flow path volume "seen" by the source of negative pressure (e.g., combined volume of the tube 140, the canister (if present), and wound dressing downstream of the source of negative pressure) is reduced when blood or tissue clots are aspirated into the fluid flow path. This reduction in volume can cause an increase (e.g., spike) in the sensed pressure signal. Such increase can have one or more characteristics indicative of the change in the flow (e.g., reduction in flow due to the presence of blood or tissue clots) of the aspirated material. For example, blood or tissue clots being aspirated into and moving through the fluid flow path, may be interspersed with pockets of liquid or gaseous exudate moving through the fluid flow path. Because liquid or gaseous exudate is less dense, it will flow more rapidly than blood or tissue clots. These changes in flow will be reflected in the sensed pressure signal as follows: during movement of denser material through the fluid flow path, the pressure signal will increase, whereas during movement of less dense material (e.g., liquid or gaseous exudate) through the fluid flow path, the pressure signal will decrease. This pattern of increased pressure followed by decreased pressure (or vice versa) can be indicative of the presence of blood or tissue clots in the fluid flow path. For example, one or more of the duration of time between pressure increases and decreases (or vice versa), actual values of increased and decreased pressure, and the like can be compared to one or more of a set of thresholds to determine whether blood or tissue clots are being aspirated into the fluid flow path.

The multiple pressure sensor values collected over a period of time can be used to determine presence of blood. For example, the rate of change of the pressure can be analyzed over the period of time by comparing the multiple determined rates of changes to one or more thresholds. If the one or more thresholds is satisfied N times (where N is an integer, such as two, three, four, or more) over the period of time, the processor can indicate that blood has been detected. Advantageously, in certain embodiments, this approach can prevent false positives due to errant pressure readings, noise, and the like.

The processor can be a processor dedicated to processing pressure sensor data from one or more of the pressure sensors and outputting one or more signals based thereon (e.g., the processor can be coupled to or mounted on the one or more pressure sensors, can be a dedicated digital signal processor (DSP), etc.), or the processor can additionally process other non-pressure sensor data and output one or more signals based thereon for the pump assembly 150.

At block 16, the processor of the pump assembly 150 can store in a memory device the determined one or more properties (such as the estimated flow rate), for instance, for later reference or outputting.

In some implementations, at least two pressure sensors can be positioned in the fluid flow path to permit differential measurement of the pressure, which can be used in addition to or instead of the rate of change to determine presence of blood. For example, a first pressure sensor can be positioned upstream of the wound (such as at or near the inlet of the negative pressure source) and a second pressure sensor can be positioned at or near the wound or at or near a canister. This configuration can be accomplished by incorporating, in addition to one or more lumens forming a first fluid flow path connecting the negative pressure source to the wound (such as the flow path), a second fluid flow path that includes one or more lumens in which the second pressure sensor is positioned.

The first and second fluid flow paths can be fluidically isolated from each other. When the at least two pressure sensors are used, the rate of change of pressure (e.g., in peak-to-peak pressure or maximum pressure) in the first and second fluid flow paths can be determined and the difference in pressure detected between the first and second pressure sensors can be determined. These values can be used separately or together to detect presence of blood in the first fluid flow path or the second fluid flow path.

For example, suppose that the first pressure sensor is positioned at or near the inlet and measures a pressure level in the canister, and the second pressure sensor is positioned at or near the wound and measures a pressure level at the wound. Further, suppose that the first pressure sensor indicates that a desired or set level of negative pressure being administered by the negative pressure source is communicated to the canister, while the second pressure sensor indicates that a lower negative pressure level (more positive pressure) is present at the wound (for instance, due to blood or blood clots being aspirated from the wound). In addition to or instead of the determined rates of change, the pressure differential between the pressure levels measured by the first and second pressure sensors can thus be used to determine and indicate presence of blood.

The level of activity of the negative pressure source, as explained herein, can be used in addition to or instead of the rate of change of pressure to determine presence of blood. When blood or blood clots enter a portion of the fluid flow path, the negative pressure source administers pressure to a smaller volume, which in turn may cause the negative pressure source to lower its activity level (e.g., to slow down a motor of the negative pressure source in the case where the negative pressure include a motor) in response to the decreased flow. This lower level of activity can be used together with or instead of determined rate of change to detect presence of blood.

OTHER VARIATIONS

In some embodiments, an apparatus for detecting compliant and non-compliant use of a negative pressure wound therapy device is disclosed. The apparatus can include a memory device and a processor. The memory device can store pressure data indicative of a magnitude of pressure over time in a fluid flow path connecting a negative pressure source and a wound dressing. The processor can be in communication with the memory device. The processor can: determine from a change in the magnitude over time whether the wound dressing was coupled to a wound when the negative pressure source provided negative pressure to the wound dressing, output a first indication in response determining that the wound dressing was coupled to the wound when the negative pressure source provided negative pressure to the wound dressing, and output a second indication different from the first indication in response determining that the wound dressing was not coupled to the wound when the negative pressure source provided negative pressure to the wound dressing.

The apparatus of the preceding paragraph can include one or more of the following features: The apparatus can further include a receiver configured to receive the pressure data via a communication network. The communication network can be a wireless communication network. The processor can compare a measure of irregularity of the change in the magnitude over time to a threshold to determine whether the wound dressing was coupled to the wound. The processor can: perform a statistical operation, a trending operation, a filtering operation, a cumulative summation operation, or a low-pass filtering operation on the magnitude over time to generate an output value; and determine that the wound dressing was coupled to the wound in response to determining that the output value is more indicative of a chaotic condition than a steady state condition. The processor can compare the magnitude over time to a pressure pattern to determine whether the wound dressing was coupled to the wound. The processor can output the second indication by outputting the second indication for presentation to a user on a graphic user interface. The processor can output the second indication by generating and transmitting an alert for presentation to a user on a graphic user interface. The processor can store, in the memory device, device usage data in association with the first indication to denote that the device usage data is associated with a compliant use of the negative pressure source. The processor can store, in the memory device, device usage data in association with the second indication to denote that the device usage data is associated with a non-compliant use of the negative pressure source.

A method of operating or manufacturing the apparatus of any of the preceding two paragraphs is disclosed.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed:

1. An apparatus for applying negative pressure, the apparatus comprising:
a negative pressure source configured to couple via a fluid flow path to a wound dressing configured to be positioned over a wound and provide negative pressure to the wound dressing;

a pressure sensor configured to monitor a pressure in the fluid flow path; and a controller configured to:

determine that the wound dressing is coupled to the wound based at least in part on the pressure in the fluid flow path and a detection of a presence of wound exudate or blood in the fluid flow path, output a first indication that the wound dressing is coupled to the wound responsive to determining that the wound dressing is coupled to the wound, determine that the wound dressing is coupled to a surface other than the wound based at least in part on the pressure in the fluid flow path and a detection of an absence of wound exudate or blood in the fluid flow path, and output a second indication that the wound dressing is uncoupled from the wound responsive to determining that the wound dressing is coupled to the surface other than the wound.

2. The apparatus of claim 1, wherein the controller is configured to:

determine that the wound dressing is coupled to the wound further based at least in part on detecting the presence of blood in the fluid flow path responsive to detecting a decrease in an activity level of the negative pressure source over a time duration.

3. The apparatus of claim 2, wherein the negative pressure source comprises a pump operated by an actuator, and the activity level comprises at least one of a pump speed of the pump, a pulse width modulation (PWM) signal configured to drive the actuator, or a current signal configured to drive the actuator.

4. The apparatus of claim 1, wherein the controller is configured to determine a first indicator associated with a change in an activity level of the negative pressure source over a time duration.

5. The apparatus of claim 4, wherein the controller is configured to perform a time series analysis to determine if the first indicator deviates from a first threshold and, based at least in part on a determination that the first indicator deviates from the first threshold, determine that the wound dressing is coupled to the wound.

6. The apparatus of claim 5, wherein the time series analysis comprises a determination of a cumulative sum (Cusum) of the first indicator.

7. The apparatus of claim 4, wherein the first indicator comprises a kurtosis of a standard deviation of the activity level, and the first indicator is indicative of a change in a flow of wound exudate in the fluid flow path.

8. The apparatus of claim 4, wherein the controller is configured to determine a cumulative sum (Cusum) of a second indicator associated with the change in the activity level over the time duration, the second indicator being different from the first indicator.

9. The apparatus of claim 8, wherein the second indicator comprises a standard deviation of the activity level indicative of a change in a gas leak rate in the fluid flow path, and the controller is configured to determine if the second indicator deviates from a second threshold and, based at least in part on a determination that the second indicator deviates from the second threshold, determine that the wound dressing is coupled to the wound.

10. The apparatus of claim 8, wherein the controller is configured to determine a Cusum of a third indicator associated with a change in the pressure in the fluid flow path over the time duration, the third indicator being different from the first indicator and the second indicator.

11. The apparatus of claim 10, wherein the third indicator comprises a mean pressure in the fluid flow path indicative of the change in the pressure in the fluid flow path over the time duration, and the controller is configured to determine if the third indicator deviates from a third threshold and, based at least in part on a determination that the third indicator deviates from the third threshold, determine that the wound dressing is coupled to the wound.

12. The apparatus of claim 1, wherein the controller is configured to determine that the wound dressing is coupled to the wound based at least in part on the pressure in the fluid flow path and the detection of the presence of wound exudate in the fluid flow path based at least in part on an activity level of the negative pressure source.

13. A method for applying negative pressure to a wound, the method comprising:

with a negative pressure source, providing via a fluid flow path negative pressure to a wound dressing configured to be positioned over a wound;

monitoring a pressure in the fluid flow path with a pressure sensor;

at a first time:

determining that the wound dressing is coupled to the wound over a first time duration based on the pressure in the fluid flow path and a detection of a presence of wound exudate or blood in the fluid flow path; and outputting a first indication that the wound dressing is coupled to the wound in response to determining that the wound dressing is coupled to the wound over the first time duration; and at a second time:

determining that the wound dressing is coupled to a surface other than the wound over a second time duration based on the pressure in the fluid flow path and a detection of an absence of wound exudate or blood in the fluid flow path; and outputting a second indication that the wound dressing is uncoupled from the wound in response to determining that the wound dressing is coupled to the surface other than the wound over the second time duration.

14. The method of claim 13, wherein said determining that the wound dressing is coupled to the wound over the first time duration comprises detecting the presence of blood in the fluid flow path responsive to detecting a decrease in an activity level of the negative pressure source over the first time duration.

15. The method of claim 14, wherein the negative pressure source comprises a pump operated by an actuator, and the activity level comprises at least one of a pump speed of the pump, a pulse width modulation (PWM) signal configured to drive the actuator, or a current signal configured to drive the actuator.

16. The method of claim 13, further comprising determining a first indicator associated with a change in an activity level of the negative pressure source over the first time duration.

17. The method of claim 13, wherein said determining that the wound dressing is coupled to the wound over the first time duration comprises determining that the wound dressing is coupled to the wound over the first time duration based at least in part on an activity level of the negative pressure source.

18. The method of claim 16, further comprising performing a time series analysis to determine that the first indicator deviates from a first threshold and determining that the wound dressing is coupled to the wound over the first time duration in response to determining that the first indicator deviates from the first threshold.

19. The apparatus of claim 1, wherein the detection of the presence of blood in the fluid flow path is performed based at least in part on an operational characteristic of at least one of the negative pressure source or the pressure sensor, and wherein the operational characteristic of at least one of the negative pressure source or the pressure sensor comprises a change in an activity level of the negative pressure source, a level of power supplied to the negative pressure source, or a rate of change of pressure in the fluid flow path.

* * * * *